(12) United States Patent
Osborne et al.

(10) Patent No.: US 11,634,754 B2
(45) Date of Patent: Apr. 25, 2023

(54) NUCLEIC ACID ENRICHMENT AND DETECTION

(71) Applicant: Biofidelity Ltd., Cambridge (GB)

(72) Inventors: Robert Osborne, Cambridge (GB); Magdalena Stolarek-Januszkiewicz, Cambridge (GB); Barnaby Balmforth, Cambridge (GB)

(*) Notice: Subject to any disclaimer, the term of this patent is extended or adjusted under 35 U.S.C. 154(b) by 0 days.

(21) Appl. No.: 17/721,691

(22) Filed: Apr. 15, 2022

(65) Prior Publication Data

US 2022/0340957 A1    Oct. 27, 2022

(30) Foreign Application Priority Data

Apr. 15, 2021 (GB) ................................ 2105388
Apr. 15, 2021 (GB) ................................ 2105405
Aug. 6, 2021 (GB) ................................ 2111381

(51) Int. Cl.
*C12Q 1/6827* (2018.01)
*C12Q 1/6806* (2018.01)
*C12Q 1/6851* (2018.01)
*C12Q 1/6876* (2018.01)

(52) U.S. Cl.
CPC ......... *C12Q 1/6827* (2013.01); *C12Q 1/6806* (2013.01); *C12Q 1/6851* (2013.01); *C12Q 1/6876* (2013.01); *C12Q 2600/156* (2013.01)

(58) Field of Classification Search
CPC ............................. C12Q 1/6876; C12Q 1/6806
See application file for complete search history.

(56) References Cited

U.S. PATENT DOCUMENTS

| | | | |
|---|---|---|---|
| 2001/0031470 A1* | 10/2001 | Shultz | C12Q 1/6823 435/91.1 |
| 2004/0009515 A1 | 1/2004 | Liu et al. | |
| 2007/0154914 A1 | 7/2007 | Gelfand et al. | |
| 2019/0271035 A1 | 9/2019 | Ding et al. | |

FOREIGN PATENT DOCUMENTS

| | | |
|---|---|---|
| EP | 2292787 | 3/2011 |
| EP | 3207982 | 8/2017 |
| EP | 3211092 | 8/2017 |
| EP | 3074529 | 5/2018 |
| WO | WO 2010/062781 | 6/2010 |
| WO | WO 2015/078831 | 6/2015 |
| WO | WO 2020/016590 | 1/2020 |
| WO | WO 2021/130494 | 7/2021 |

OTHER PUBLICATIONS

International Search Report and Written Opinion for PCT/IB2022/000217, dated Aug. 25, 2022, 18 pages.
Liu et al., PAP: detection of ultra rare mutations depends on P* oligonucleotides: "sleeping beauties" awakened by the kiss of pyrophosphorolysis. Hum Mutat. May 2004;23(5):426-36.
Liu et al., Pyrophosphorolysis-activated polymerization (PAP): application to allele-specific amplification. Biotechniques. Nov. 2000;29(5):1072-6, 1078.
Silva et al., Single-copy detection of somatic variants from solid and liquid biopsy. 11:6068.

* cited by examiner

*Primary Examiner* — Teresa E Strzelecka
(74) *Attorney, Agent, or Firm* — David A. Casimir; Casimir Jones, S.C.

(57) ABSTRACT

Disclosed is a hybridisation capture method based on the pyrophosphorolysis reaction. According to the present invention, there is provided a method for increasing the ratio of a first nucleic add sequence to second nucleic add sequence in a sample.

9 Claims, 8 Drawing Sheets

Specification includes a Sequence Listing.

SEQUENCE LISTING

<160> NUMBER OF SEQ ID NOS: 59

<210> SEQ ID NO 1
<211> LENGTH: 60
<212> TYPE: DNA
<213> ORGANISM: Artificial sequence
<220> FEATURE:

<223> OTHER INFORMATION: Synthetic

<400> SEQUENCE: 1
tttttttttt ttttttttac cttatacacc gtgccgaacg caccggagcc cagcactttg    60

<210> SEQ ID NO 2
<211> LENGTH: 100
<212> TYPE: DNA
<213> ORGANISM: Artificial sequence
<220> FEATURE:
<223> OTHER INFORMATION: Synthetic

<400> SEQUENCE: 2
cccaaccaag ctctcttgag gatcttgaag gaaactgaat tcaaaaagat caaagtgctg    60
ggctccggtg cgttcggcac ggtgtataag gtaaggtccc                         100

<210> SEQ ID NO 3
<211> LENGTH: 100
<212> TYPE: DNA
<213> ORGANISM: Artificial sequence
<220> FEATURE:
<223> OTHER INFORMATION: Synthetic

<400> SEQUENCE: 3
cccaaccaag ctctcttgag gatcttgaag gaaactgaat tcaaaaagat caaagtgctg    60
gcctccggtg cgttcggcac ggtgtataag gtaaggtccc                         100

<210> SEQ ID NO 4
<211> LENGTH: 27
<212> TYPE: DNA
<213> ORGANISM: Artificial sequence
<220> FEATURE:
<223> OTHER INFORMATION: Synthetic

<400> SEQUENCE: 4
cccaaccaag ctctcttgag gatcttg                                        27

<210> SEQ ID NO 5
<211> LENGTH: 26
<212> TYPE: DNA
<213> ORGANISM: Artificial sequence
<220> FEATURE:
<223> OTHER INFORMATION: Synthetic

<400> SEQUENCE: 5
gggaccttac cttatacacc gtgccg                                         26

<210> SEQ ID NO 6
<211> LENGTH: 89
<212> TYPE: DNA
<213> ORGANISM: Homo sapiens

<400> SEQUENCE: 6
catctgcctc acctccaccg tgcagctcat cacgcagctc atgcccttcg gctgcctcct    60
ggactatgtc cgggaacaca aagacaata                                      89

<210> SEQ ID NO 7
<211> LENGTH: 90
<212> TYPE: DNA
<213> ORGANISM: Homo sapiens

-continued

<400> SEQUENCE: 7
cgtactggtg aaaacaccgc aggctcatca tgcagctcat gcccttcggc tgcctcctgg    60
actggaagag aaagaatacc atgcagaagg                                      90

<210> SEQ ID NO 8
<211> LENGTH: 56
<212> TYPE: DNA
<213> ORGANISM: Artificial sequence
<220> FEATURE:
<223> OTHER INFORMATION: Synthetic

<400> SEQUENCE: 8
tttttttttt tttttttttt tccaggaggc agccgaaggg catgagctgc atgatg        56

<210> SEQ ID NO 9
<211> LENGTH: 39
<212> TYPE: DNA
<213> ORGANISM: Artificial sequence
<220> FEATURE:
<223> OTHER INFORMATION: Synthetic

<400> SEQUENCE: 9
gcctccctcg cgccatcagc atctgcctca cctccaccg                            39

<210> SEQ ID NO 10
<211> LENGTH: 41
<212> TYPE: DNA
<213> ORGANISM: Artificial sequence
<220> FEATURE:
<223> OTHER INFORMATION: Synthetic

<400> SEQUENCE: 10
gccttgccag cccgctcaga tattgtcttt gtgttcccgg a                         41

<210> SEQ ID NO 11
<211> LENGTH: 23
<212> TYPE: DNA
<213> ORGANISM: Artificial sequence
<220> FEATURE:
<223> OTHER INFORMATION: Synthetic

<400> SEQUENCE: 11
acgtactggt gaaaacaccg cag                                             23

<210> SEQ ID NO 12
<211> LENGTH: 24
<212> TYPE: DNA
<213> ORGANISM: Artificial sequence
<220> FEATURE:
<223> OTHER INFORMATION: Synthetic

<400> SEQUENCE: 12
gcctccttct gcatggtatt cttt                                            24

<210> SEQ ID NO 13
<211> LENGTH: 56
<212> TYPE: DNA
<213> ORGANISM: Artificial sequence
<220> FEATURE:
<223> OTHER INFORMATION: Synthetic

<400> SEQUENCE: 13
tttttttttt tttttttttt tccaggaggc agccgaaggg catgagctgc atgatg        56

```
<210> SEQ ID NO 14
<211> LENGTH: 145
<212> TYPE: DNA
<213> ORGANISM: Homo sapiens

<400> SEQUENCE: 14
ctggtccctc attgcactgt actcccatct gcctcacctc caccgtgcag ctcatcacgc      60
agctcatgcc cttcggctgc ctcctggact atgtccggga acacaaagac aatatgtgtc     120
gagaatatcc aagagacagg tttct                                           145

<210> SEQ ID NO 15
<211> LENGTH: 150
<212> TYPE: DNA
<213> ORGANISM: Homo sapiens

<400> SEQUENCE: 15
ctggtccctc attgcactgt actccacgta ctggtgaaaa caccgcaggc tcatcatgca      60
gctcatgccc ttcggctgcc tcctggactg gaagagaaag aataccatgc agaaggaggc     120
gtgtcgagaa tatccaagag acaggtttct                                      150

<210> SEQ ID NO 16
<211> LENGTH: 30
<212> TYPE: DNA
<213> ORGANISM: Artificial sequence
<220> FEATURE:
<223> OTHER INFORMATION: Synthetic

<400> SEQUENCE: 16
agaaacctgt ctcttggata ttctcgacac                                       30

<210> SEQ ID NO 17
<211> LENGTH: 25
<212> TYPE: DNA
<213> ORGANISM: Artificial sequence
<220> FEATURE:
<223> OTHER INFORMATION: Synthetic

<400> SEQUENCE: 17
ctggtccctc attgcactgt actcc                                            25

<210> SEQ ID NO 18
<211> LENGTH: 42
<212> TYPE: DNA
<213> ORGANISM: Artificial sequence
<220> FEATURE:
<223> OTHER INFORMATION: Synthetic

<400> SEQUENCE: 18
gccttgccag cccgctcaga tattgtcttt gtgttccgg ac                          42

<210> SEQ ID NO 19
<211> LENGTH: 39
<212> TYPE: DNA
<213> ORGANISM: Artificial sequence
<220> FEATURE:
<223> OTHER INFORMATION: Synthetic

<400> SEQUENCE: 19
gcctccctcg cgccatcagc atctgcctca cctccaccg                             39

<210> SEQ ID NO 20
<211> LENGTH: 23
```

```
<212> TYPE: DNA
<213> ORGANISM: Artificial sequence
<220> FEATURE:
<223> OTHER INFORMATION: Synthetic

<400> SEQUENCE: 20
acgtactggt gaaaacaccg cag                                              23

<210> SEQ ID NO 21
<211> LENGTH: 24
<212> TYPE: DNA
<213> ORGANISM: Artificial sequence
<220> FEATURE:
<223> OTHER INFORMATION: Synthetic

<400> SEQUENCE: 21
gcctccttct gcatggtatt cttt                                             24

<210> SEQ ID NO 22
<211> LENGTH: 157
<212> TYPE: DNA
<213> ORGANISM: Homo sapiens

<400> SEQUENCE: 22
aatgatacgg cgaccaccga gatctacact ggtaattacc gacgaaaacg gcccgtgcag       60
ctcatcacgc agctcatgcc cttcggctgc ctcctggact atgtccggga accgcaagac      120
tgtaaccacg cgtatctcgt atgccgtctt ctgcttg                               157

<210> SEQ ID NO 23
<211> LENGTH: 157
<212> TYPE: DNA
<213> ORGANISM: Homo sapiens

<400> SEQUENCE: 23
caagcagaag acggcatacg agatacgcgt ggttacagtc ttgcggttcc cggacatagt       60
ccaggaggca gccgaagggc atgagctgcg tgatgagctg cacgggccgt tttcgtcggt      120
aattaccagt gtagatctcg gtggtcgccg tatcatt                               157

<210> SEQ ID NO 24
<211> LENGTH: 160
<212> TYPE: DNA
<213> ORGANISM: Homo sapiens

<400> SEQUENCE: 24
aatgatacgg cgaccaccga gatctacaca tgaaagctgg ctacaggaag gctcaaaaag       60
atcaaagtgc tgggctccgg tgcgttcggc acggtgtata aggtaaggtc ccaatattga      120
aacccacggc atggtgatct cgtatgccgt cttctgcttg                            160

<210> SEQ ID NO 25
<211> LENGTH: 160
<212> TYPE: DNA
<213> ORGANISM: Homo sapiens

<400> SEQUENCE: 25
caagcagaag acggcatacg agatcaccat gccgtgggtt tcaatattgg gaccttacct       60
tatacaccgt gccgaacgca ccggagccca gcactttgat cttttttgagc cttcctgtag     120 ccagctttca tgtgtagatc tcggtggtcg ccgtatcatt                            160

<210> SEQ ID NO 26
```

```
<211> LENGTH: 146
<212> TYPE: DNA
<213> ORGANISM: Homo sapiens

<400> SEQUENCE: 26
aatgatacgg cgaccaccga gatctacacc agccgccgcg gtaagatcac agattttggg      60
ctggccaaac tgctgggtgc ggaagagaaa gaataccatg cagagaattg gcggggagc     120 acatctcgta tgccgtcttc tgcttg                                          146

<210> SEQ ID NO 27
<211> LENGTH: 146
<212> TYPE: DNA
<213> ORGANISM: Homo sapiens

<400> SEQUENCE: 27
caagcagaag acggcatacg agatgtgctc ccccgccaat tctctgcatg gtattctttc      60
tcttccgcac ccagcagttt ggccagccca aaatctgtga tcttaccgcg gcggctggtg    120
tagatctcgg tggtcgccgt atcatt                                          146

<210> SEQ ID NO 28
<211> LENGTH: 160
<212> TYPE: DNA
<213> ORGANISM: Homo sapiens

<400> SEQUENCE: 28
aatgatacgg cgaccaccga gatctacacg gaagtgaaaa gtcgtaacaa ggcatgattt      60
tggtctagct acagtgaaat ctcgatggag tgggtcccat cagtttgaac agttctgcat    120
cgatgaagaa cgcagcatct cgtatgccgt cttctgcttg                           160

<210> SEQ ID NO 29
<211> LENGTH: 160
<212> TYPE: DNA
<213> ORGANISM: Homo sapiens

<400> SEQUENCE: 29
caagcagaag acggcatacg agatgctgcg ttcttcatcg atgcagaact gttcaaactg      60
atgggaccca ctccatcgag atttcactgt agctagacca aaatcatgcc ttgttacgac    120
ttttcacttc cgtgtagatc tcggtggtcg ccgtatcatt                           160

<210> SEQ ID NO 30
<211> LENGTH: 156
<212> TYPE: DNA
<213> ORGANISM: Homo sapiens

<400> SEQUENCE: 30
aatgatacgg cgaccaccga gatctacaca ggcgctgttt ggtctcttag ccaggaagca      60
tacgtgatgg ctggtgtggg ctccccatat gtctcccgcc ttctgggcat caggaatcat    120
tagcggtagc gaatctcgta tgccgtcttc tgcttg                               156

<210> SEQ ID NO 31
<211> LENGTH: 156
<212> TYPE: DNA
<213> ORGANISM: Homo sapiens
```

<400> SEQUENCE: 31
caagcagaag acggcatacg agattcgcta ccgctaatga ttcctgatgc ccagaaggcg    60
ggagacatat ggggagccca caccagccat cacgtatgct tcctggctaa gagaccaaac   120
agcgcctgtg tagatctcgg tggtcgccgt atcatt                              156

<210> SEQ ID NO 32
<211> LENGTH: 157
<212> TYPE: DNA
<213> ORGANISM: Homo sapiens

<400> SEQUENCE: 32
aatgatacgg cgaccaccga gatctacacg agccggtagt gttgaaagga ggtccatcat    60
ctctgcggtg gttggcattc tgctggtcgt ggtcttgggg gtggtctttg gctttgcctg   120
cactcattga aggatctcgt atgccgtctt ctgcttg                             157

<210> SEQ ID NO 33
<211> LENGTH: 157
<212> TYPE: DNA
<213> ORGANISM: Homo sapiens

<400> SEQUENCE: 33
caagcagaag acggcatacg agatccttca atgagtgcag gcaaagccaa agaccacccc    60
caagaccacg accagcagaa tgccaaccac cgcagagatg atggacctcc tttcaacact   120
accggctcgt gtagatctcg gtggtcgccg tatcatt                             157

<210> SEQ ID NO 34
<211> LENGTH: 155
<212> TYPE: DNA
<213> ORGANISM: Homo sapiens

<400> SEQUENCE: 34
aatgatacgg cgaccaccga gatctacact ggctcaggaa gaacgcagtt gtggtagttg    60
gagctggtgg cgtaggcaag agtgccttga cgatacagct aattcagatg gagcatgtgg   120
tttaattgcg aatctcgtat gccgtcttct gcttg                               155

<210> SEQ ID NO 35
<211> LENGTH: 155
<212> TYPE: DNA
<213> ORGANISM: Homo sapiens

<400> SEQUENCE: 35
caagcagaag acggcatacg agattcgcaa ttaaaccaca tgctccatct gaattagctg    60
tatcgtcaag gcactcttgc ctacgccacc agctccaact accacaactg cgttcttcct   120
gagccagtgt agatctcggt ggtcgccgta tcatt                               155

<210> SEQ ID NO 36
<211> LENGTH: 170
<212> TYPE: DNA
<213> ORGANISM: Homo sapiens

<400> SEQUENCE: 36
aatgatacgg cgaccaccga gatctacacc cttggtcatt tagaggaagt ggctactggt    60
ccctcattgc actgtactcc tcttgacctg ctgtgtcgag aatatccaag agacaggttt   120
ctccatgcat cgatgaagaa cgcagcatct cgtatgccgt cttctgcttg              170

<210> SEQ ID NO 37
<211> LENGTH: 170
<212> TYPE: DNA
<213> ORGANISM: Homo sapiens

<400> SEQUENCE: 37
caagcagaag acggcatacg agatgctgcg ttcttcatcg atgcatggag aaacctgtct    60
cttggatatt ctcgacacag caggtcaaga ggagtacagt gcaatgaggg accagtagcc   120
acttcctcta aatgaccaag ggtgtagatc tcggtggtcg ccgtatcatt              170

<210> SEQ ID NO 38
<211> LENGTH: 156
<212> TYPE: DNA
<213> ORGANISM: Homo sapiens

<400> SEQUENCE: 38
aatgatacgg cgaccaccga gatctacact gatttccgtg cgtctgaatg cccgtgcagc    60
tcatcatgca gctcatgccc ttcggctgcc tcctggacta tgtccgggaa ccgaaacacg   120
ctacggcagc atatctcgta tgccgtcttc tgcttg                             156

<210> SEQ ID NO 39
<211> LENGTH: 156
<212> TYPE: DNA
<213> ORGANISM: Homo sapiens

<400> SEQUENCE: 39
caagcagaag acggcatacg agatatgctg ccgtagcgtg tttcggttcc cggacatagt    60
ccaggaggca gccgaagggc atgagctgca tgatgagctg cacgggcatt cagacgcacg   120
gaaatcagtg tagatctcgg tggtcgccgt atcatt                             156

<210> SEQ ID NO 40
<211> LENGTH: 157
<212> TYPE: DNA
<213> ORGANISM: Homo sapiens

<400> SEQUENCE: 40
aatgatacgg cgaccaccga gatctacacg ttgaaaatgg tctgctgctg ttcaaaaaga    60
tcaaagtgct ggcctccggt gcgttcggca cggtgtataa ggtaaggtcc ctctgtggtg   120
gatgaagcca ataatctcgt atgccgtctt ctgcttg                            157

<210> SEQ ID NO 41
<211> LENGTH: 157
<212> TYPE: DNA
<213> ORGANISM: Homo sapiens

<400> SEQUENCE: 41
caagcagaag acggcatacg agattattgg cttcatccac cacagaggga ccttacctta    60
tacaccgtgc cgaacgcacc ggaggccagc actttgatct ttttgaacag cagcagacca   120
ttttcaacgt gtagatctcg gtggtcgccg tatcatt                            157

<210> SEQ ID NO 42
<211> LENGTH: 157
<212> TYPE: DNA

<400> SEQUENCE: 42
aatgatacgg cgaccaccga gatctacacg cggtaattcc agctccaagt gatcacagat     60
tttgggcgtg ccaaactgct gggtgcggaa gagaaagaat accatgcaga gagaggtgca    120
aattctggga tctatctcgt atgccgtctt ctgcttg                             157

<210> SEQ ID NO 43
<211> LENGTH: 157
<212> TYPE: DNA
<213> ORGANISM: Homo sapiens

<400> SEQUENCE: 43
caagcagaag acggcatacg agatagatcc cagaatttgc acctctctct gcatggtatt     60
ctttctcttc cgcacccagc agtttggcac gcccaaaatc tgtgatcact ggagctgga    120 attaccgcgt gtagatctcg gtggtcgccg tatcatt                             157

<210> SEQ ID NO 44
<211> LENGTH: 156
<212> TYPE: DNA
<213> ORGANISM: Homo sapiens

<400> SEQUENCE: 44
aatgatacgg cgaccaccga gatctacacg catcgatgaa gaacgcagct gattttggtc     60
tagctacaga gaaatctcga tggagtgggt cccatcagtt tgaacagttg tcgcatatca    120
ataagcggag gaatctcgta tgccgtcttc tgcttg                             156

<210> SEQ ID NO 45
<211> LENGTH: 156
<212> TYPE: DNA
<213> ORGANISM: Homo sapiens

<400> SEQUENCE: 45
caagcagaag acggcatacg agattcctcc gcttattgat atgcgacaac tgttcaaact     60
gatgggaccc actccatcga gatttctctg tagctagacc aaaatcagct gcgttcttca    120
tcgatgcgtg tagatctcgg tggtcgccgt atcatt                             156

<210> SEQ ID NO 46
<211> LENGTH: 155
<212> TYPE: DNA
<213> ORGANISM: Homo sapiens

<400> SEQUENCE: 46
aatgatacgg cgaccaccga gatctacact ggctagtggc attctgatgc ggaagcatac     60
gtgatggctg tgtgtgtggg ctccccatat gtctcccgcc ttctgggcat gcaagggcgg    120
ctaaagtatc aatctcgtat gccgtcttct gcttg                              155

<210> SEQ ID NO 47
<211> LENGTH: 155
<212> TYPE: DNA
<213> ORGANISM: Homo sapiens

<400> SEQUENCE: 47
caagcagaag acggcatacg agattgatac tttagccgcc cttgcatgcc cagaaggcgg     60
gagacatatg gggagcccac acacacagcc atcacgtatg cttccgcatc agaatgccac    120
tagccagtgt agatctcggt ggtcgccgta tcatt                              155

<210> SEQ ID NO 48
<211> LENGTH: 159
<212> TYPE: DNA
<213> ORGANISM: Homo sapiens

<400> SEQUENCE: 48
aatgatacgg cgaccaccga gatctacact gcaatgagga ccggtatatc tctgtccatc    60
atctctgcgg tggaaggcat tctgctggtc gtggtcttgg gggtggtctt tggtggaata   120
ttaacacggg cgtgcatctc gtatgccgtc ttctgcttg                          159

<210> SEQ ID NO 49
<211> LENGTH: 159
<212> TYPE: DNA
<213> ORGANISM: Homo sapiens

<400> SEQUENCE: 49
caagcagaag acggcatacg agatgcacgc ccgtgttaat attccaccaa agaccacccc    60
caagaccacg accagcagaa tgccttccac cgcagagatg atggacagag atataccggt   120
cctcattgca gtgtagatct cggtggtcgc cgtatcatt                          159

<210> SEQ ID NO 50
<211> LENGTH: 153
<212> TYPE: DNA
<213> ORGANISM: Homo sapiens

<400> SEQUENCE: 50
aatgatacgg cgaccaccga gatctacacg aggacaggat tagatacccg gttgtggtag    60
ttggagcttg tggcgtaggc aagagtgcct tgacgataca gctaattcag aggaaggtgg   120
ggatgacgta tctcgtatgc cgtcttctgc ttg                                153

<210> SEQ ID NO 51
<211> LENGTH: 153
<212> TYPE: DNA
<213> ORGANISM: Homo sapiens

<400> SEQUENCE: 51
caagcagaag acggcatacg agatacgtca tccccacctt cctctgaatt agctgtatcg    60
tcaaggcact cttgcctacg ccacaagctc caactaccac aaccgggtat ctaatcctgt   120
cctcgtgtag atctcggtgg tcgccgtatc att                                153

<210> SEQ ID NO 52
<211> LENGTH: 165
<212> TYPE: DNA
<213> ORGANISM: Homo sapiens

<400> SEQUENCE: 52
aatgatacgg cgaccaccga gatctacacg ctcaggaaga acgctggtac tggtccctca    60
ttgcactgta ctcctcgtga cctgctgtgt cgagaatatc caagacagg gtttctccat   120 cgaagtacat gtgtagcggt gatctcgtat gccgtcttct gcttg                   165

<210> SEQ ID NO 53
<211> LENGTH: 165
<212> TYPE: DNA
<213> ORGANISM: Homo sapiens

```
<400> SEQUENCE: 53
caagcagaag acggcatacg agatcaccgc tacacatgta cttcgatgga gaaacctgtc    60
tcttggatat tctcgacaca gcaggtcacg aggagtacag tgcaatgagg gaccagtacc   120
agcgttcttc ctgagcgtgt agatctcggt ggtcgccgta tcatt                   165

<210> SEQ ID NO 54
<211> LENGTH: 29
<212> TYPE: DNA
<213> ORGANISM: Artificial sequence
<220> FEATURE:
<223> OTHER INFORMATION: Synthetic

<400> SEQUENCE: 54
aatgatacgg cgaccaccga gatctacac                                      29

<210> SEQ ID NO 55
<211> LENGTH: 29
<212> TYPE: DNA
<213> ORGANISM: Artificial sequence
<220> FEATURE:
<223> OTHER INFORMATION: Synthetic

<400> SEQUENCE: 55
aatgatacgg cgaccaccga gatctacac                                      29

<210> SEQ ID NO 56
<211> LENGTH: 23
<212> TYPE: DNA
<213> ORGANISM: Artificial sequence
<220> FEATURE:
<223> OTHER INFORMATION: Synthetic

<400> SEQUENCE: 56
tggtaattac cgacgaaaac ggc                                            23

<210> SEQ ID NO 57
<211> LENGTH: 21
<212> TYPE: DNA
<213> ORGANISM: Artificial sequence
<220> FEATURE:
<223> OTHER INFORMATION: Synthetic

<400> SEQUENCE: 57
acgcgtggtt acagtcttgc g                                              21

<210> SEQ ID NO 58
<211> LENGTH: 22
<212> TYPE: DNA
<213> ORGANISM: Artificial sequence
<220> FEATURE:
<223> OTHER INFORMATION: Synthetic

<400> SEQUENCE: 58
tgatttccgt gcgtctgaat gc                                             22

<210> SEQ ID NO 59
<211> LENGTH: 21
<212> TYPE: DNA
<213> ORGANISM: Artificial sequence
<220> FEATURE:
<223> OTHER INFORMATION: Synthetic
```

<400> SEQUENCE: 59
atgctgccgt agcgtgtttc g                            21

NUCLEIC ACID ENRICHMENT AND DETECTION

The present application claims priority to GB Application Nos 2105405.1, filed Apr. 15, 2021, 2105388.9, filed Apr. 15, 2021, and 2111381.6, filed Aug. 6, 2021, the disclosures of which are herein incorporated by reference in their entireties.

SEQUENCE LISTING

The text of the computer readable sequence listing filed herewith, titled "40018-201_SEQUENCE_LISTING_ST25", created Apr. 15, 2022, having a file size of 15,464 bytes, is hereby incorporated by reference in its entirety.

FIELD OF THE INVENTION

Targeted detection of low frequency variants in a pool of wild-type molecules is clinically important for early detection of cancer, monitoring of cancer progression, targeting of cancer therapies, non-invasive prenatal testing, monitoring of T-cell populations that target particular (neo-)antigens, and for early warning of organ transplant rejection. A combination of hybridisation-capture and next-generation sequencing (NGS) is the most commonly applied method for targeted and multiplex detection of low frequency variants but has several suboptimal characteristics. In general, hybridisation capture enriches for target regions of interest but not for variant molecules. This results in the vast majority of sequencing reads deriving from wild-type rather than variant molecules. This is wasteful, adds cost, and makes it difficult to detect rare variants against the background of errors from storage, library preparation and sequencing. This results in NGS having insufficient specificity for routine detection of variants below ~0.1%. Modified library preparation methods (such as duplex sequencing) can increase specificity, yielding accurate sequencing data from single molecules. Unfortunately, methods like duplex sequencing also reduce sensitivity (for example, by modifying library preparation methods to avoid end-repair and by deliberately imposing molecular bottlenecks). The method described here allows enrichment of variant molecules located within target regions of interest, using, for example, a modified hybridisation capture method based on pyrophosphorolysis (PPL). This both reduces the number of sequencing reads that are required but also opens the door to multiplexed detection of low frequency variant molecules below the current limit of detection of NGS.

SUMMARY

In some embodiments, provided herein is a hybridisation method based on a pyrophosphorolysis reaction. These methods harness the double-strand specificity of pyrophosphorolysis; a reaction which will not proceed efficiently with single-stranded oligonucleotide substrates or double-stranded substrates which include blocking groups of nucleotide mismatches.

For example, in some embodiments, provided herein are methods that comprise contacting a sample (e.g., containing two or more different nucleic acid molecules) with a probe and pyrophosphorolysis reaction reagents and enriching for or depleting a first nucleic acid molecule relative to a second nucleic acid molecule based on different complementarity of the probe to the first and second nucleic acid molecules, resulting in different levels of pyrophosphorolysis of the probe when hybridized to the first and second nucleic acid molecules.

For example, in some embodiments, the method comprises enriching for or depleting a first nucleic acid molecule in a sample that comprises a mixture of nucleic acid molecules, by contacting the first nucleic acid molecule with a probe that differs in complementary to a target region on the first nucleic acid molecule relative to other nucleic acid molecules in the sample; conducting a pyrophosphorolysis reaction; and enriching for or depleting the first nucleic acid molecule. In some embodiments, the probe has greater complementary to the target region of the first nucleic acid molecule than it does to a corresponding target region of a second nucleic acid in the sample. In some embodiments, the probe has lesser complementary to the target region of the first nucleic molecule than it does to a corresponding target region of a second nucleic acid in the sample. In some embodiments, the first nucleic acid and the second nucleic acid differ by a sequence variation (e.g., a point mutation, a deletion, an insertion, multinucleotide change, fusion, etc.). In some embodiments, the probe includes a sequence that is perfectly complementary to the target region of the sequence of greater complementarity and has one or more mismatches to a sequence variation found in the corresponding target region of the sequence of lesser complementarity. In some embodiments, the probe contains one or more mismatches to the target regions of both the first and second nucleic acid molecules, but contains more mismatches to the target region of the nucleic acid of lesser complementarity. In particular, the probe is designed such that the degree of pyrophosphorolysis differs when the probe is hybridized to a first nucleic acid relative to a second nucleic acid, permitting selective enrichment or depletion of the first nucleic acid relative to the second nucleic acid based on the different reaction product generated by the pyrophosphorolysis.

For example, in some embodiments, provided herein are methods for increasing or decreasing the ratio of a first nucleic acid sequence to a second nucleic acid sequence in a sample, comprising: a) exposing a sample, comprising the first and second nucleic acid sequences, to a probe that differs in complementarity to the first and second nucleic acid sequences; b) conducting a pyrophosphorolysis reaction; and c) enriching for or depleting the first nucleic acid sequence relative to the second nucleic acid sequence.

In some embodiments of the present invention, there is provided a method for increasing the ratio of a first nucleic acid sequence to second nucleic acid sequence in a sample, wherein the sample comprises at least a first and second sequence, the method comprising the steps of:
a. introducing the sample comprising one or more nucleic acid analytes to a first reaction mixture comprising:
   i. a single-stranded probe oligonucleotide $A_O$ having differential complementarity to the first and second nucleic acid sequences (e.g., wherein the 3' end of said probe is perfectly complementary to one of the first or second sequence but imperfectly complementary to the other);
b. introducing the reaction mixture produced by step (a) to a second reaction mixture comprising:
   ii. a pyrophosphorolysing enzyme; and
   iii. a source of pyrophosphate ion
wherein $A_O$ anneals (e.g., perfectly) to one of the nucleic acid sequences to create an at least partially double-stranded intermediate product in which $A_O$ (e.g., the 3' end of $A_O$) forms a double-stranded complex with said sequence and $A_O$ is pyrophosphorolysed in the 3'-5' direction from its 3'-end, whilst any $A_0$ that has annealed less perfectly (e.g., imperfectly) to the other sequence is pyrophosphorolysed in the 3'-5' direction to a lesser extent due to said less perfect (e.g., imperfect) annealing;

c. separating any $A_0$ sequence complexes which were more perfectly (e.g., perfectly) annealed by:
  iv. allowing the strands of said complex to separate (e.g., melt apart) as a consequence of the pyrophosphorolysis reaction; or
  v. heating the reaction mixture to a temperature sufficient for the strands of said complex to separate (e.g., melt apart) but which is below the temperature required for the strands of any $A_0$ which less perfectly (e.g., imperfectly) annealed to separate (e.g., melt apart); and d. separating $A_0$, and thereby any nucleic acid sequences remaining annealed thereto, from any nucleic acid sequences not annealed to $A_0$.

Probes may be provided with one or more components that are removed prior to or during the pyrophosphorolysis reaction. For example, probes may be provided with a non-complementary flap or other blocking group at their 3' end that prevents initiation of a pyrophosphorolysis or polymerase reaction until the blocking group is removed. The blocking group may be removed by any suitable mechanism (e.g., enzymatic cleavage, chemical reaction, temperature shift, etc.). The sequence of the probe that provides the differential pyrophosphorolysis products, when hybridized to distinct nucleic acid molecules, may be positioned at any suitable location in the initial probe. For example, a mismatch sequence may be positioned at the 3' terminal base of the 3' end of the probe. A mismatch sequence may be positioned internally in the probe at the 3' end. A mismatch sequence may be positioned centrally in the probe. A mismatch sequence may be positioned within the 5' half of the probe.

The 5' end of the probe may comprise a region (e.g., a 5' tail) that acts as an identifier (e.g., a sample identifier). Such a sequence finds use, for example, to selectively pull down captured molecules from a specific sample or specific region one-by-one from a mixed sample. Such identifiers may find particular use in multiplex regions where multiple different targets are undergoing reactions in the same sample or same reaction vessel.

The analytes/sequences to which the method of the invention can be applied are those nucleic acids, such as naturally-occurring or synthetic DNA or RNA molecules, which include the target polynucleotide sequence(s) being sought. In some embodiments, the analytes/sequences will typically be present in an aqueous solution containing it and other biological material and in some embodiments the analytes/sequences will be present along with other background nucleic acid molecules which are not of interest for the purposes of the test. In some embodiments, the analytes/sequences will be present in low amounts relative to these other nucleic acid components. Preferably, for example where the analyte is derived from a biological specimen containing cellular material, prior to performing step (i) of the method some or all of these other nucleic acids and extraneous biological material will have been removed using sample-preparation techniques such as filtration, centrifuging, chromatography or electrophoresis.

The compositions and methods of the invention may be employed against any type of sample, including, but not limited to environmental (e.g., water, soil, air, etc.) samples and biological samples. Biological samples may be from any source including plants, animals, infectious disease agents, and the like. Suitably, in some embodiments, the analytes/sequences are derived from a biological sample taken from a mammalian subject (especially a human patient) such as blood, plasma, sputum, urine, skin, biopsy or surgical resection. In some embodiments, the biological sample will be subjected to lysis in order that the analytes/sequences are released by disrupting any cells present. In other embodiments, the analytes/sequences may already be present in free form within the sample itself; for example cell-free DNA circulating in blood or plasma. The compositions and methods of the invention find particular use with historically challenging sample types that may have low allele fractions of the analyte of interest. Such samples include blood, urine, cytosponge-collected samples (e.g., oesophageal samples), bronchoalveolar lavage (BAL) derived samples, pleural fluid, and cerebrospinal fluid (CSF).

In some embodiments, samples are pooled samples. Pooled samples involve mixing multiple samples togethers in a batch where the pooled collection is tested. This approach increases the number of individual samples that can be tested using a more limited amount of resources. Pooled samples of interest include, but are not limited to, donated blood samples, agricultural samples, food samples, sperm samples, and biological samples tested for the presence of infectious disease agents (e.g., SARS-CoV-2, HIV, HCV, etc.). In some embodiments, the pooled sample is an environmentally collected sample (e.g., wastewater sample) that has, by the nature of its generation, pooled samples from multiple different sources. While pooling of samples may reduce the allele fraction of variants as the samples dilute each other, it can provide a dramatic increase in efficiency of screening. Because the technology provided herein enables detection at very low allele fractions, it is particularly well suited for analysis of pooled samples. In some embodiments, a fraction of each initial sample is pooled without use of barcodes or other complex preparation steps and the pooled sample is tested. If a positive result is obtained, remaining fractions of the unpooled samples may be tested individually.

Also provided herein are compositions (e.g., reagents, kits, reactions mixture, instruments, software) that find use with the methods described herein. For example, in some embodiments, provided here are compositions comprising one or more reagents necessary, sufficient, or useful for conducting a method as described herein. For example, in some embodiments, compositions comprise: one or more oligonucleotides A0, wherein A0 comprises: a sequence (e.g., 3' end) which is differentially complementary to a known first sequence and a known second sequence (e.g., perfectly complementary to a known first sequence but imperfectly complementary to a known second sequence); one or more pyrophosphorolysing enzymes; and one or more sources of pyrophosphate ions. In some embodiments, the compositions further comprise a target nucleic acid isolation component that segregates target nucleic acid molecules that are more perfectly (e.g., perfectly) complementary to said probe (e.g., 3' end of said probe) from nucleic acid molecules less perfectly (e.g., imperfectly) complementary to said probe (e.g., 3' end of said probe) following a pyrophosphorolysis reaction. In some embodiments, the compositions comprise one or more solid supports. In some embodiments, the compositions comprise one or more buffers. In some embodiments, A0 comprises a 5' tail region which is not complementary to either a known first or known second sequence. In some embodiments, A0 further comprises a capture moiety. In some embodiments, the composition further comprises one or more capture oligonucleotide $C_0$ which comprises a capture moiety and wherein a 5' tail region of A0 is complementary to a region of $C_0$. In some embodiments, the capture moiety is biotin and the solid support comprises streptavidin. In some embodiments, the solid support comprises a capture oligonucleotide $C_0$ and wherein a 5' tail region of $A_0$ is complementary to a region of $C_0$. In some embodiments, the solid support is a bead (e.g., magnetic or paramagnetic bead). In some embodiments, the composition further comprises one or more epigenetic modification sensitive or dependent restriction enzymes. In some embodiments, the composition further comprises one or more restriction endonucleases. In some embodiments, the composition further comprises one or more transposomes. In some embodiments, the composition comprises a Cas protein (e.g., Cas9). In some embodiments, the composition further comprises one or more transposases. In some embodiments, the composition further comprises one or more ligases. In some embodiments, the composition further comprises one or more blocking oligonucleotides. In some embodiments, the one or more blocking oligonucleotides are resistant to pyrophosphorolysis. In some embodiments, the composition further comprises reagents for conducting an amplification (e.g., PCR), sequencing (e.g., next generation sequencing), or detection reaction. In some embodiments, the composition further comprises one or more molecular probes. In some embodiments, the one or more molecular probes are fluorescently labelled. In some embodiments, the $A_0$ (e.g., 3' end of the $A_0$) is more complementary (e.g., perfectly complementary) to a wild type sequence of the human genome and less complementary (e.g., imperfectly complementary) to a mutant allele of said wild type sequence. In some embodiments, the $A_0$ (e.g., 3' end of the $A_0$) is less complementary (e.g., imperfectly complementary) to a wild type sequence of the human genome and more complementary (e.g., perfectly complementary) to a mutant allele of said wild type sequence. In some embodiments, the composition further comprises components for the transcription of RNA into cDNA.

In some embodiments, the composition is a reaction mixture comprising a reaction, at a particular time point, of any of the methods described herein. In some embodiments, the reaction mixture is present prior to pyrophosphorolysis. In some embodiments, the reaction mixture is present during pyrophosphorolysis. In some embodiments, the reaction mixture is present after pyrophosphorolysis. In some embodiments, the reaction mixture comprises probe/nucleic acid hybridization complexes of the methods described herein. In some embodiments, the reaction mixture comprises captured nucleic acid molecules of the method described herein. In some embodiments, the reaction mixture comprises regions comprising concentrations of a desired target nucleic that are higher or lower than the concentration of the desired target nucleic that was present in a sample that underwent a pyrophosphorolysis reaction. For example, in some embodiments, provided herein are reaction mixtures comprising: a sample; pyrophosphorolysis reagents at pyrophosphorolyzing concentrations (i.e., reagents concentrations that favor pyrophosphorolysis); a first nucleic acid molecule from the sample hybridized to a probe having a sequence, wherein a discrimination region of the probe is complementary to the first nucleic acid molecule; and a second nucleic acid molecule from the sample hybridized a probe having said sequence, wherein the discrimination region of the probe is not perfectly complementary to the second nucleic acid molecule. In some embodiments, provided herein is a reaction mixture comprising a sample; pyrophosphorolysis reagents at pyrophosphorolyzing concentrations; and a first nucleic acid molecule in a first region of the reaction mixture, wherein the first nucleic acid has a higher or lower concentration in the first region than the concentration of the first nucleic acid in the sample.

Also provided herein are uses of the compositions (e.g., uses of the kits, uses of the reaction mixtures, uses of the reagents, uses of the instruments, uses of the software). For example, provided herein are uses of the composition for enriching or depleting a target nucleic acid in a sample.

In some embodiments, provided herein are devices and instruments that find use in the methods described herein. In some embodiments, the devices and instrument find use to collect and distribute samples into reaction vessels. In some embodiments, the devices and instruments provide reaction chambers for conducting the methods. In some embodiments, the devices and instruments provide multiple zones or regions (e.g., wells, channels, etc) for housing a reaction and/or for isolating enriched desired target nucleic acids or depleting desired target nucleic acids. In some embodiments, the devices and instruments find use to amplify or sequence nucleic acid molecules. In some embodiments, the devices and instruments find use to detect nucleic acid molecules. In some embodiments, the devices and instruments find use to receive or transmit information from a user. For example, the devices and instrument may comprise a user interface to receive user instructions and a display to visually present results to a user.

In some embodiments, provided herein are computing devices. The computing devices find use to control instruments or devices to facilitate the methods described herein. In some embodiments, the computing devices collect, analyse, and report data. In some embodiments, the computing devices comprise one or more processors that run a computer program. In some embodiments, the computing devices comprise non-transitory computer readable media (e.g., software) comprising instructions that direct a processor to carry out one or more of the computing steps.

BRIEF DESCRIPTION OF THE DRAWINGS

FIG. 6A. Graph shows detection of T790M variant from 0-50% VAF. FIG. 6B. Zoom in on detection of 0.1% VAF.

DETAILED DESCRIPTION OF THE INVENTION

Figure 1:
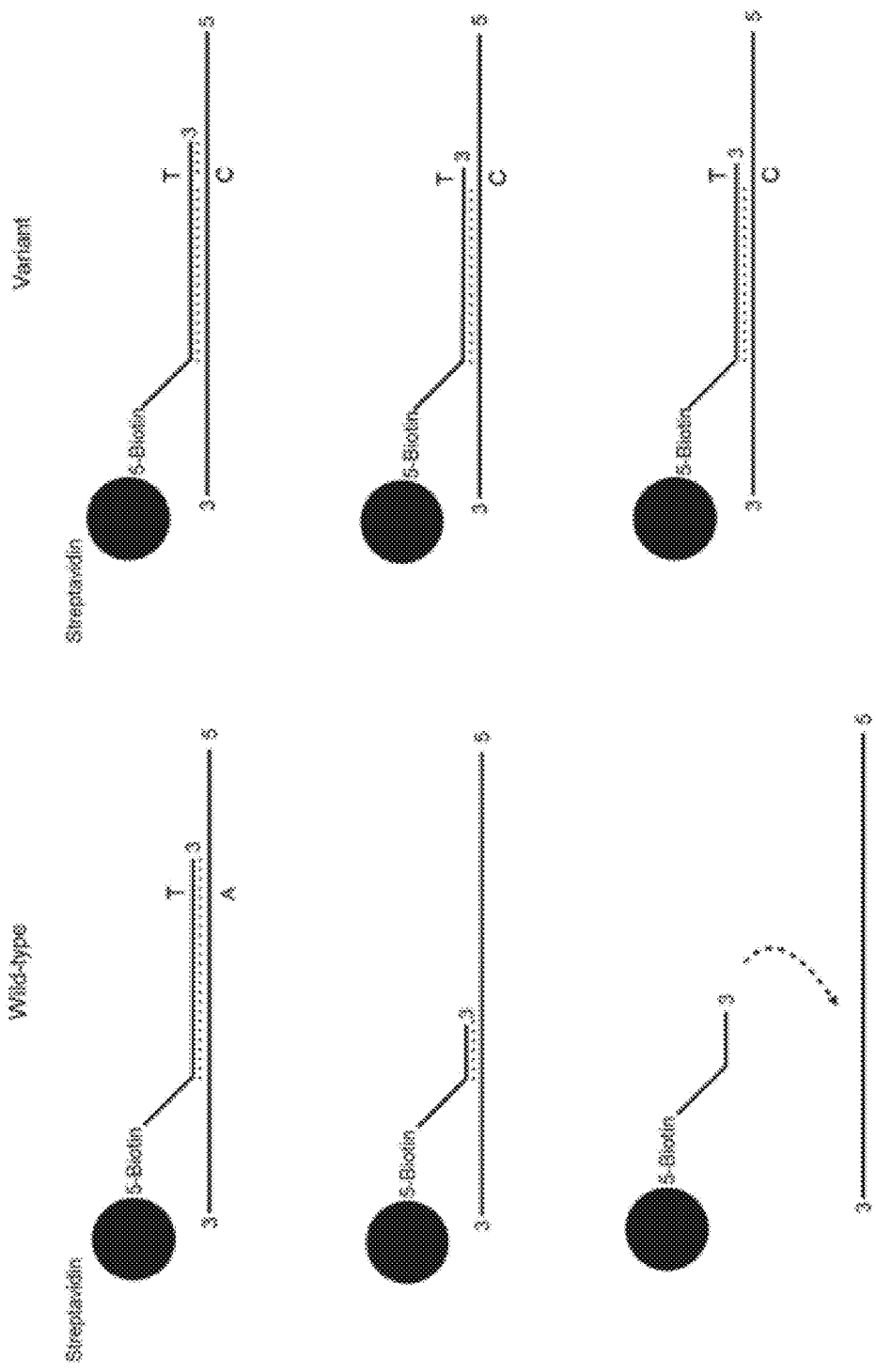
FIG. 1: A schematic representation of one embodiment of the invention wherein biotinylated probes are pre-bound to streptavidin coated paramagnetic beads. The bead-bound probes are then hybridised to target DNA and undergo pyrophosphorolysis. In this example, bead-bound probes are perfectly complementary to a wild-type sequence and imperfectly complementary/mismatched to a variant sequence. Probes hybridised to wild-type sequences are pyrophosphorolysed and the wild-type DNA is released from beads into solution, whilst probes hybridised to variant sequences are mismatched and so are not pyrophosphorolysed to the same extent as wild-type sequences, resulting in the variant sequences remaining bead bound. Variant sequences may then then be identified, in one example by sequencing.
Figure 2:
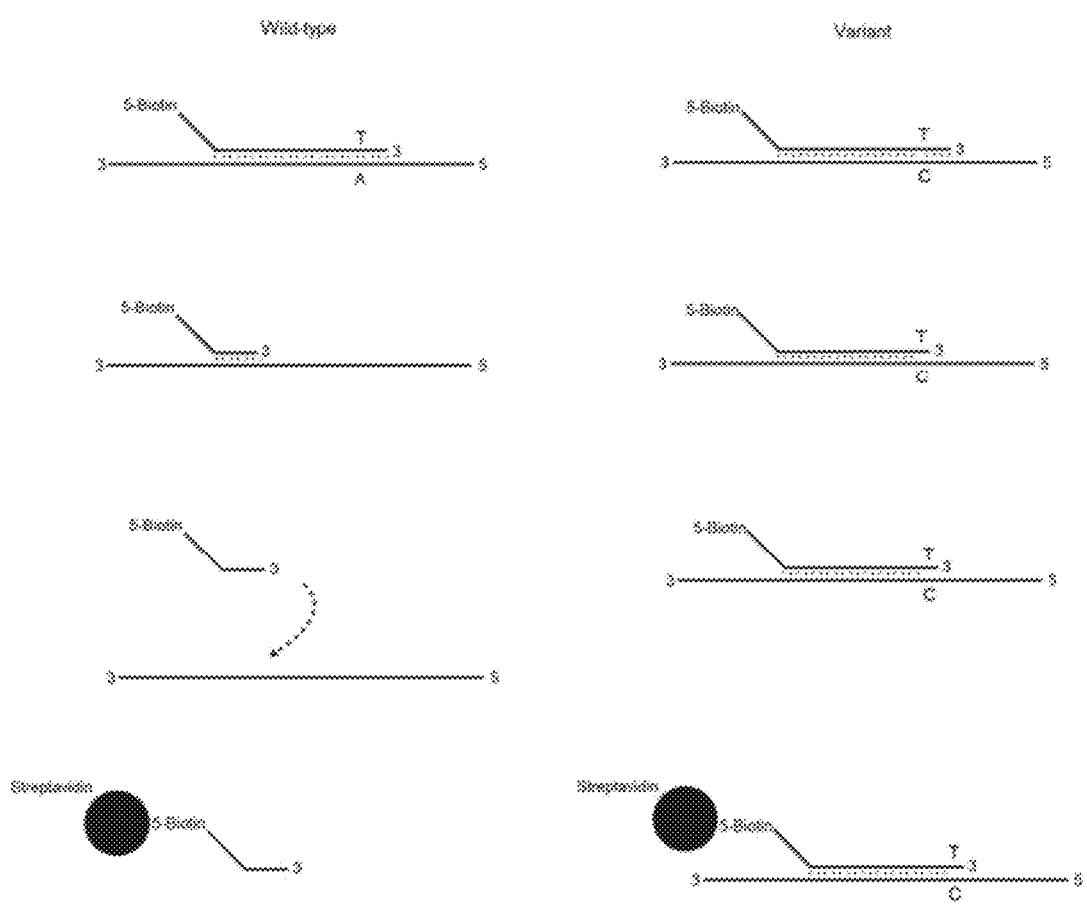
FIG. 2: A schematic representation of one embodiment of the invention wherein biotinylated probes are hybridised to target DNA, undergo pyrophosphorolysis and are then captured onto streptavidin paramagnetic beads. In this example, probes are perfectly complementary to a wild-type sequence and imperfectly complementary/mismatched to a variant sequence. Probes hybridised to wild-type sequences are pyrophosphorolysed and the wild-type DNA is released from the probe whilst probes hybridised to mismatched variant sequences are not pyrophosphorolysed to the same extent as wild-type sequences and the variant sequences thus remain probe bound. Probes are then captured onto streptavidin paramagnetic beads, with only variant sequences therefore becoming bead-bound. Variant sequences may then then be identified, in one example by sequencing.
Figure 3:
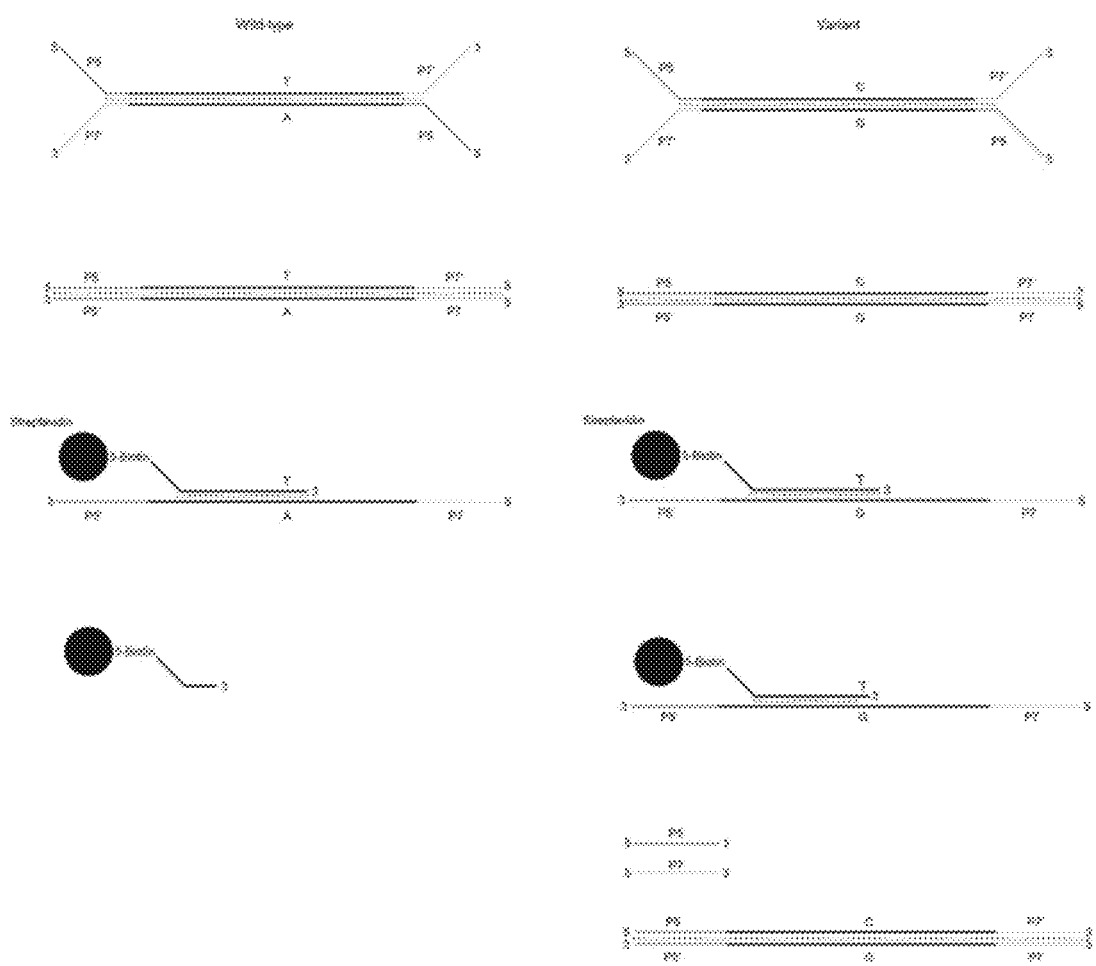
FIG. 3: A schematic representation of one embodiment of the invention according to that described in FIG. 1 wherein prior to hybridisation of probe to target DNA, the target DNA undergoes adaptor tagging and amplification by PCR. Following hybridisation, probes undergo pyrophosphorolysis and adaptor tagged variant sequences remain bead-bound. Bead-bound variant sequences then undergo amplification by PCR.

In some embodiments, the present method uses pyrophosphorolysis as way of enriching for or depleting desired nucleic acid sequences. The pyrophosphorolysis reaction relies on complementarity between hybridised strands, and hence only digests strands without or with fewer mismatches. The reaction selectively shortens certain sequences which are complementary, whilst leaving mismatched sequences less digested. The reaction can be performed such that molecules hybridized to the shortened sequences are recovered and analysed. Alternatively, the reaction can be performed such that less shortened sequences are analysed. Alternatively, the reaction can be performed so that the sequences which have not undergone any pyrophosphorolysis are analysed.

The enrichment or depletion may be repeated one or more times to further enrich a sample for the sequence of interest. For example, in some embodiments, a second round of enrichment or depletion occurs after the first round is completed using the same reagents as the first round. In other embodiments, a different probe is used that is selective for a different sequence of the target nucleic acid that is to be enriched for or removed. This approach is particularly well suited in instances where the sequence to be enriched or depleted differs from the sequence to be eliminated by at least two base positions. For example, a target nucleic acid containing two polymorphisms relative to wild type may undergo a first round of enrichment or depletion based on the first polymorphism and a second round of enrichment or depletion based on the second polymorphism. Exponential levels of enrichment or depletion may be achieved by employing multiple rounds. In some embodiments, a target nucleic acid is modified to generate a synthetic sequence (e.g., addition of a polymorphism), prior to enrichment or depletion, such that the synthetic sequence is targeted for enrichment or depletion relative to sequences not containing the synthetic sequence. In some embodiments, two or more nucleic acids may be enriched for or depleted in any given round of the reaction by use of multiple probes. In some embodiments, a particular nucleic acid may be enriched for while a second nucleic acid may be depleted in one or more rounds of the reaction.

In an aspect of the present invention, there is provided a method for altering the ratio of a first nucleic acid sequence to a second nucleic acid sequence in a sample, wherein the sample comprises at least a first and second sequence, the method comprising the steps of:
a. introducing the sample comprising one or more nucleic acid analytes to a first reaction mixture comprising:
  i. a single-stranded probe oligonucleotide $A_0$ wherein the probe is differentially complementary to first and second sequences (e.g., the 3' end or other region of said probe is perfectly complementary to one of the first or second sequence but imperfectly complementary to the other);
  ii. a pyrophosphorolysing enzyme; and
  iii. a source of pyrophosphate ion;
wherein $A_0$ anneals (e.g., perfectly) to the first nucleic acid sequence to create an at least partially double-stranded intermediate product in which the $A_0$ (e.g., the 3' end of $A_0$) forms a double-stranded complex with said sequence and $A_0$ is pyrophosphorolysed in the 3'-5' direction from its 3' end, whilst any $A_0$ that has annealed less well (e.g., imperfectly) to the second sequence is pyrophosphorolysed in the 3'-5' direction to a lesser extent due to said lesser (e.g., imperfect) annealing;
b. selectively denaturing any shortened $A_0$ sequence complexes which were better (e.g., perfectly) annealed to the first sequence; and
c. separating $A_0$, and thereby any second nucleic acid sequences remaining annealed thereto, from the first nucleic acid sequences not annealed to $A_0$, thereby altering the ratio of the first nucleic acid sequence to the second nucleic acid sequence.

In an aspect of the present invention, there is provided a method for increasing the ratio of a first nucleic acid sequence to a second nucleic acid sequence in a sample, wherein the sample comprises at least a first and second sequence, the method comprising the steps of:
a. introducing the sample comprising one or more nucleic acid analytes to a first reaction mixture comprising:
  i. a single-stranded probe oligonucleotide $A_0$ wherein said probe (e.g., the 3' end of or other region of said probe) is more complementary (e.g., perfectly complementary) to one of the first or second sequence but less complementary (e.g., imperfectly complementary) to the other;

b. introducing the reaction mixture produced by step (a) to a second reaction mixture comprising:
   ii. a pyrophosphorolysing enzyme; and
   iii. a source of pyrophosphate ion
wherein $A_0$ anneals (e.g., perfectly) to one of the nucleic acid sequences to create an at least partially double-stranded intermediate product in which the $A_0$ (e.g., the 3' end of $A_0$) forms a double-stranded complex with said sequence and $A_0$ is pyrophosphorolysed in the 3'-5' direction from its 3'-end, whilst any $A_0$ that has annealed less well (e.g., imperfectly) to the other sequence is pyrophosphorolysed in the 3'-5' direction to a lesser extent due to said lower (e.g., imperfect) annealing;

c. separating any $A_0$ sequence complexes which were better (e.g., perfectly) annealed by:
   i. allowing the strands of said complex to separate (e.g., melt apart) as a consequence of the pyrophosphorolysis reaction; or
   ii. heating the reaction mixture to a temperature sufficient for the strands of said complex to separate (e.g., melt apart) but which is below the temperature required for the strands of any $A_0$ which annealed less well (e.g., imperfectly) to separate (e.g., melt apart); and d. separating $A_0$, and thereby any nucleic acid sequences remaining annealed thereto, from any nucleic acid sequences not annealed to $A_0$.

In some embodiments, the separation of any $A_0$ sequence complexes which were better (e.g., perfectly) annealed occurs by using reaction conditions that favour $A_0$ sequence complexes which were better (e.g., perfectly) annealed over $A_0$ sequence complexes with less (e.g., imperfect) annealing. This could take the form of changes to the reaction mixture temperature and/or changes to the pH of the reaction mixture and/or changes to the salinity of the reaction mixture.

In some embodiments, the first and second reaction mixtures are combined such that the first reaction mixture of step (a) further comprises a pyrophosphorolysing enzyme and a source of pyrophosphate ion.

In some embodiments, $A_0$ which anneals better (e.g., perfectly) to one of the nucleic acid sequences to form a double-stranded complex is pyrophosphorolysed to such an extent that the double-stranded complex separates (e.g., melts), separating the shortened $A_0$ from the nucleic acid sequence. $A_0$ which less well (e.g., imperfectly) annealed to the other sequence remains in a double-stranded complex with said sequence.

In some embodiments, the reaction mixture can be heated to denature. Thus double-stranded complexes comprising $A_0$ sequences which were better (e.g., perfectly) annealed, and thus more completely pyrophosphorolysed, separate (e.g., melt apart) whilst those double-stranded complexes comprising $A_0$ which were less well (e.g., imperfectly) annealed, and pyrophosphorolysed less, remain double-stranded due to such complexes possessing a higher melting temperature as a result of more complementary base-pairs remaining.

In some embodiments, the pH of the reaction mixture can be raised to denature. Thus double-stranded complexes comprising $A_0$ sequences which were better (e.g., perfectly) annealed, and thus more completely pyrophosphorolysed, denature whilst those double-stranded complexes comprising $A_0$ which were less well (e.g., imperfectly) annealed, and pyrophosphorolysed less, remain double-stranded due to such complexes possessing more complementary base-pairs and requiring an even higher pH to become denatured.

In some embodiments, the salt concentration of the reaction mixture is lowered. Thus double-stranded complexes comprising $A_0$ sequences which were better (e.g., perfectly) annealed, and thus more completely pyrophosphorolysed, denature whilst those double-stranded complexes comprising $A_0$ which were less well (e.g., imperfectly) annealed, and pyrophosphorolysed less, remain double-stranded due to such complexes possessing more complementary base-pairs and requiring an even lower salt concentration to become denatured.

In some embodiments, chemical agents (e.g., dimethylsulfoxide (DMSO), formamide, etc.) are employed to denature nucleic acids to facilitate enrichment or depletion.

In some embodiments, nucleic acid molecules (displacing oligonucleotides) and enzymes or proteins are used separate hybridized nucleic acid molecules.

In some embodiments, two or more of the following characteristics of the reaction mixture are altered such that separation of double-stranded complexes comprising $A_0$ sequences which were better (e.g., perfectly) annealed occurs whilst double-stranded complexes comprising $A_0$ which were less well (e.g., imperfectly) annealed remain hybridised:
   the pH of the reaction mixture;
   the temperature of the reaction mixture;
   the salt concentration of the reaction mixture;
   addition of chemical denaturing agents.

In some embodiments, capture of $A_0$ onto a solid support occurs prior to, or following, step (a). In some embodiments, the separation in step (d) is performed through capture of $A_0$ onto a solid support prior to, or following, step (a).

In some embodiments, $A_0$ further comprises a 5' tail region which is not complementary to either of the sequences.

In some embodiments, two probes are employed, one for the forward strand of a target and one for the reverse stand. In some embodiments, it is beneficial to design the probes so that they do not hybridise to each other to form a construct capable of undergoing pyrophosphorolysis (e.g., they have 3' overhangs when they hybridize to each other).

In some embodiments, the capture onto the solid support is performed through hybridisation of the 5' tail region of $A_0$ to another oligo, $C_0$, which comprises a capture moiety through which it is bound to the solid support either before or after hybridisation to $A_0$.

In some embodiments, $A_0$ further comprises a capture moiety through which it is bound to the solid support.

In some embodiments, the capture moiety is biotin and the solid support comprises streptavidin.

In some embodiments, $A_0$ is extended in the reaction with biotinylated nucleotides for subsequent capture.

In some embodiments, a diphosphohydrolase enzyme (e.g., Apyrase) is provided in the methods or compositions of the invention. The diphosphohydrolase enzyme hydrolyses released nucleotides from the pyrophosphorolysis reaction, maintaining optimal pyrophosphorolysis reaction conditions.

In some embodiments, inorganic pyrophosphatase enzyme is provided in the methods or compositions of the inventions. Inorganic pyrophosphatase removes pyrophosphate ions after pyrophosphorolysis and before subsequent steps where the presence of pyrophosphate ions may be undesired or suboptimal.

The technology is not limited to the use of capture to partition or enrich for nucleic acid molecules of interest.

Molecules may be partitioned or enriched, for example, based on differences in size, charge, or shape or other physical or chemical properties. In some embodiments, a moiety is added to the nucleic acid of interest (e.g., via click chemistry modification), whereby the added moiety imparts a selectable distinguishing characteristic to the nucleic acid of interest.

In some embodiments, the solid support is a bead.

In some embodiments, the bead is a magnetic or paramagnetic bead.

In some embodiments, one or more wash steps are performed between one or more of the steps.

In some embodiments, wash and hybridisation steps are performed at elevated temperatures between 25-95° C.

In some embodiments, the sample is an adaptor tagged library of nucleic acid analytes.

In some embodiments, following step (d), either the nucleic acids that remain annealed to $A_0$, or those not annealed to $A_0$, are identified.

In some embodiments, the sequences are identified by an amplification reaction (e.g., polymerase chain reaction (PCR), nucleic acid sequence-based amplification (NASBA), multiple displacement amplification (MDA), transcription-mediated amplification (TMA), strand displacement amplification (SDA), rolling circle amplification (RCA), loop mediated isothermal amplification (LAMP), recombinase polymerase amplification (RPA), helicase dependent amplification (HDA), nicking and extension amplification reaction (NEAR), and the like).

in some embodiments, the sequences are identified by isothermal identification.

In some embodiments, the sequences are identified by PCR.

In some embodiments, the sequences are identified by microarray analysis.

In some embodiments, the sequences are identified by sequencing.

In some embodiments, the sequences are identified by Next Generation Sequencing (NGS) (e.g., bridge amplification sequencing (Illumina), SMRT sequencing (PacBio), Ion Torrent sequencing, nanopore sequencing, pyrosequencing, and the like).

In some embodiments, multiple different probe oligonucleotides $A_0$ are employed, each with different sequences (e.g., 3' end sequences) designed to anneal (e.g., perfectly anneal) to a different target sequence, and wherein the concentrations of multiple target sequences are simultaneously increased relative to non-target sequences.

In some embodiments, the different probe oligonucleotides $A_0$ have sequences (e.g., 3' end sequences) which anneal (e.g., perfectly anneal) to sequences of the human genome that include genetic variants associated with the presence, treatment, or monitoring of disease.

In some embodiments, after step (d) the presence or absence of said genetic variants in the sample analyte is inferred through the identification of nucleic acid sequences which have annealed to, and subsequently been released from, $A_0$, and the presence or absence of disease is thereby inferred.

In some embodiments, after step (d) the presence or absence of said genetic variants in the sample analyte is inferred through the identification of nucleic acid sequences which have annealed to, and subsequently been released from, $A_0$, and the appropriate treatment for a disease is thereby inferred.

In some embodiments, after step (d) the presence or absence of said genetic variants in the sample analyte is inferred through the identification of nucleic acid sequences which have annealed to, and subsequently been released from, $A_0$, and the response of a patient to a specific disease treatment is thereby inferred.

In some embodiments, after step (d) the presence or absence of said genetic variants in the sample analyte is inferred through the identification of nucleic acid sequences which have annealed to, and subsequently been released from, $A_0$, and one or more patient treatment decisions are made based on the presence of absence of said genetic variants.

In some embodiments, the sample is a human blood or tissue sample.

In some embodiments, the disease is a cancer.

In some embodiments, the cancer is lung cancer.

In some embodiments, one or more hybridisation steps are performed between one or more of the steps.

In some embodiments, the nucleic acid analysed is a methylated sequence or is derived from a methylated sequence. The technology is used to differentiate methylation status at any particular or multiple locations in a target nucleic acid. Methylated sequences may first be modified using chemical treatments (e.g., oxidation, reduction, bisulfite treatment) or by exposure to methylation dependent restriction enzymes or any other suitable approach followed by enrichment and/or identification of the modified sequence.

In some embodiments, nucleic acid sequences present in the sample are bisulfite treated prior to step (a) of the method.

In some embodiments, nucleic acid sequences present in the sample are bisulfite treated following step (a) of the method.

In some embodiments, nucleic acid sequences present in the sample are treated enzymatically to convert cytosines to uracil prior to step (a) of the method.

In some embodiments, nucleic acid sequences present in the sample are treated enzymatically to convert cytosines to uracil following step (a) of the method.

In some embodiments, nucleic acid sequences present in the sample are exposed to epigenetic-dependent/sensitive restriction enzymes prior to step (a) of the method.

In some embodiments, nucleic acid sequences present in the sample are exposed to epigenetic-dependent/sensitive restriction enzymes following step (a) of the method.

In some embodiments, targeted regions of RNA present in the sample are transcribed into DNA prior to step (a) of the method.

In some embodiments, targeted regions of RNA present in the sample are transcribed into DNA following step (a) of the method.

In some embodiments, there is provided a method of capturing a target nucleic acid sequence of interest from a sample comprising at least a first and second sequence comprising the steps of:
  a. introducing the sample comprising one or more nucleic acid analytes to a first reaction mixture comprising:
    i. a single-stranded probe oligonucleotide $A_0$ wherein said probe contains a sequence (e.g., at the 3' end or elsewhere) that is complementary (e.g., perfectly complementary) to one of the first or second sequence but less complementary (e.g., imperfectly complementary) to the other;
  b. introducing the reaction mixture produced by step (a) to a second reaction mixture comprising:
    i. a pyrophosphorolysing enzyme; and
    ii. a source of pyrophosphate ion wherein $A_O$ anneals (e.g., perfectly anneals) to one of the nucleic acid sequences to create an at least partially double-stranded intermediate product in which $A_O$ (e.g., the 3' end of $A_O$) forms a double-stranded complex with said sequence and $A_O$ is pyrophosphorolysed in the 3'-5' direction from its 3'-end, whilst any $A_O$ that has annealed to a lesser extent (e.g., imperfectly) to the other sequence is pyrophosphorolysed in the 3'-5' direction to a lesser extent due to said lesser (e.g., imperfect) annealing;

c. separating any $A_O$ sequence complexes which were annealed (e.g., perfectly annealed) by:
  i. allowing the strands of said complex to separate (e.g., melt apart) as a consequence of the pyrophosphorolysis reaction; or
  ii. heating the reaction mixture to a temperature sufficient for the stands of said complex to separate (e.g., melt apart) but which is below the temperature required for the stands of any $A_O$ which is less well annealed (e.g., imperfectly annealed) to separate (e.g., melt apart); and
d. separating $A_O$, and thereby any nucleic acid sequences remaining annealed thereto, from any nucleic acid sequences not annealed to $A_O$.

In some embodiments, the solid support is a polymer and/or resin coated solid surface.

In some embodiments, the solid support is a polystyrene solid support.

In some embodiments, polystyrene $(C_8H_8)$, is a polymer wherein n is 10, 20, 30, 40, 50, 100, 150, 200, 250, 300, 350, 400, 450, 500, 550, 600, 650, 700, 750, 800, 850, 900, 950, 1,000, 1,250, 1,500, 1,750, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 12,500, 15,000, 16,000, 17,000, 17,500, 18,000, 19,000, 20,000, 25,000, 30,000, 40,000, 50,000, 60,000, 70,000, 80,000, 90,000, 100,000 or more, or where n is any integer between any of these points, or n is within any range derivable between any two of these points, is utilised.

In some embodiments, the polystyrene solid support is a particle, micro particle, magnetic bead, magnetic microparticle, paramagnetic bead, paramagnetic microparticle, resin or any particulate that comprises polystyrene polymers.

In some embodiments, the polystyrene support is modified to include one or more of the following functional groups: amine, carboxylate, sulfonate, trimethylamine and/or epoxide.

In some embodiments, the solid support is a magnetic or paramagnetic bead.

In some embodiments, the magnetic or paramagnetic bead is a shape which maximises the surface area of said bead.

In some embodiments, the magnetic or paramagnetic bead is a regular shape.

In some embodiments, the magnetic or paramagnetic bead is an irregular shape.

In some embodiments, the magnetic or paramagnetic bead has a diameter of less than, or equal to: 1000, 900, 800, 700, 600, 500, 400, 300, 200, 100, 90, 80, 70, 60, 50, 40, 30, 20, 10, 5, 2.5, 1, 0.5, 0.25 or 0.1 micron.

In some embodiments, the solid support is a magnetic or paramagnetic polystyrene bead.

In some embodiments, the magnetic or paramagnetic polystyrene bead comprises iron oxide.

In some embodiments, the magnetic or paramagnetic polystyrene bead is Streptavidin-coupled.

In some embodiments, the solid support is a Streptavidin-coupled Dynabead (RTM).

In some embodiments, the solid support is a dextran-modified surface.

In some embodiments, the dextran-modified surface is a particle, micro particle, magnetic or paramagnetic bead, resin or any particulate that comprises dextran polymers.

In some embodiments, the dextran polymers have an approximate molecular weight from 1000 to 410000.

In some embodiments, the dextran polymers have an approximate molecular weight from 25000 to about 100000.

In some embodiments, the dextran-surface modified is further modified to include one or more functional groups.

In some embodiments, the dextran-modified surface is modified to include one or more of the following functional groups: amine, carboxylate, sulfonate, trimethylamine and/or epoxide.

In some embodiments, the solid support is a magnetic or paramagnetic bead.

In some embodiments, the magnetic or paramagnetic bead is a shape which maximises the surface area of said bead.

In some embodiments, the magnetic or paramagnetic bead is a regular shape.

In some embodiments, the magnetic or paramagnetic bead is an irregular shape.

In some embodiments, the magnetic or paramagnetic bead has a diameter of less than, or equal to: 1000, 900, 800, 700, 600, 500, 400, 300, 200, 100, 90, 80, 70, 60, 50, 40, 30, 20, 10, 5, 2.5, 1, 0.5, 0.25 or 0.1 micron.

In some embodiments, the magnetic or paramagnetic bead is a dextran magnetic bead selected from: Nanomag® Dextran (ND); Nanomag® Dextran-SO3H (ND-503H); BioMag® Dextran-Coated Charcoal; or BioMag® Plus Dextran.

In some embodiments, the solid support is a Polyethylene Glycol (PEG) or PEG-modified surface.

In some embodiments, the Polyethylene Glycol (PEG) or PEG-modified surface is a particle, micro particle, magnetic or paramagnetic bead, resin or any particulate that comprises PEG.

In some embodiments of the invention PEG, $(CH_2O)_n$, is a polymer wherein n is 10, 20, 30, 40, 50, 100, 150, 200, 250, 300, 350, 400, 450, 500, 550, 600, 650, 700, 750, 800, 850, 900, 950, 1,000, 1,250, 1,500, 1,750, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 12,500, 15,000, 16,000, 17,000, 17,500, 18,000, 19,000, 20,000, 25,000, 30,000, 40,000, 50,000, 60,000, 70,000, 80,000, 90,000, 100,000 or more, or where n is any integer between any of these points, or n is within any range derivable between any two of these points, is utilised.

In some embodiments, the PEG utilised is PEG-200, PEG-300, PEG-400, PEG-600, PEG-1000, PEG-1300-1600, PEG-1450, PEG-3000-3700, PEG-3500, PEG-6000, PEG-8000 or PEG-17500.

In some embodiments, wherein the Polyethylene Glycol (PEG) or PEG-modified surface is a magnetic or paramagnetic microparticle or bead, the microparticle or bead is selected from Nanomag® PEG-300 (Plain) or Nanomag®-D.

In some embodiments, the solid support is a Polyvinylpyrrolidone (PVP) or PVP-modified surface.

In some embodiments, the PVP or PVP-modified surface is a particle, micro particle, magnetic or paramagnetic bead, resin or any particulate that comprises PVP.

In some embodiments of the invention PVP, n-vinyl pyrrolidone, is a polymer wherein n is 10, 20, 30, 40, 50, 100, 150, 200, 250, 300, 350, 400, 450, 500, 550, 600, 650, 700, 750, 800, 850, 900, 950, 1,000, 1,250, 1,500, 1,750, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 12,500, 15,000, 16,000, 17,000, 17,500, 18,000, 19,000, 20,000, 25,000, 30,000, 40,000, 50,000, 60,000, 70,000, 80,000, 90,000, 100,000 or more, or where n is any integer between any of these points, or n is within any range derivable between any two of these points, is utilised.

In some embodiments, the solid support is a polysaccharide or polysaccharide-modified surface.

In some embodiments, the polysaccharide or polysaccharide-modified surface is a particle, micro particle, magnetic or paramagnetic bead, resin or any particulate that comprises a polysaccharide.

In some embodiments, the polysaccharide is selected from one or more of dextran, ficoll, glycogen, gum arabic, xanthan gum, carageenan, amylose, agar, amylopectin, xylans and/or beta-glucans.

In some embodiments, the solid support is a chemical resin or chemical resin-modified surface.

In some embodiments, the chemical resin or chemical-resin modified surface is selected from one or more of the following resins: isocyanate, glycerol, piperidino-methyl, polyDMAP (polymer-bound dimethyl 4-aminopyridine), DIPAM (Diisopropylaminomethyl, aminomethyl, polystyrene aldehyde, tris(2-aminomethyl) amine, morpholino-methyl, BOBA (3-Benzyloxybenzaldehyde), triphenylphosphine or benzylthio-methyl.

In some embodiments, the capture moiety is covalently attached to the solid support via a chemically-cleavable linker, such as a disulfide, allyl, or azide-masked hemiaminal ether linker.

In some embodiments, the capture moiety is covalently attached to the solid support via amide or phosphorothioate bonds.

The person skilled in the art will appreciate that there exists a plethora of techniques for the covalent and non-covalent immobilisation of oligonucleotides to solid supports, see for example "Strategies for Attaching Oligonucleotides to Solid Supports." (2014) produced by Integrated DNA Technologies (IDT®).

In some embodiments, the capture moiety comprises an oligonucleotide sequence and the solid support comprises oligonucleotides bearing the complementary sequence.

In some embodiments, the oligonucleotide sequence comprises one or more modified bases and/or other such modifications known to the person skilled in the art, to change the melting temperature.

In some embodiments, the presence of one or more modified bases and/or other such modifications known to the person skilled in the art leads to a decrease in the melting temperature.

In some embodiments, the presence of one or more modified bases and/or other such modifications known to the person skilled in the art leads to an increase in the melting temperature.

In some embodiments, the length of the complementary sequence is between 10, 20, 30, 40, 50, 100, 150 and 200 bases.

In some embodiments, the length of the complementary sequence is between 10, 20, 30, 40, 50, and 100 bases.

In some embodiments, the length of the complementary sequence is between 10-20, 10-30, 10-40 and 10-50 bases.

In some embodiments, the length of the complementary sequence is between 10-20, 10-30 and 10-40 bases.

In some embodiments, the length of the complementary sequence is between 10-20 and 10-30 bases.

In some embodiments, the length of the complementary sequence is between 10-20 bases.

In some embodiments, the capture moiety comprises a chemical modification and is attached to the solid support via an interaction between the chemical modification and the solid support.

In some embodiments, the chemical modification is biotin and the solid support further comprises streptavidin.

In some embodiments, captured oligonucleotide sequences are released from the solid support.

In some embodiments, captured oligonucleotide sequences are released from the solid support by chemical denaturation.

In some embodiments, chemical denaturation is achieved by the use of suitable concentration of base.

in some embodiments, 0.1M of NaOH may be used.

In some embodiments, oligonucleotide sequences are released from the solid support by the cleavage of a chemical linker through the addition of tris(2-carboxyethyl)phosphine (TCEP) or dithiothreitol (DTT) for a disulfide linker; palladium complexes or an allyl linker; or TCEP for an azide-masked hemiaminal ether linker.

In some embodiments, oligonucleotide sequences are released from the solid support by removing a non-canonical base, from oligonucleotide sequences, and cleavage at the resultant abasic site. In some embodiments, the non-canonical base is uracil, which is removed by uracil DNA glycosylase. In an alternate embodiment, the non-canonical base is 8-oxoguanine, which is removed by formamidopyrimidine DNA glycosylase (Fpg).

In some embodiments, the capture moiety is an oligonucleotide region and release is performed through heating of the reaction mixture.

In some embodiments, the reaction mixture is heated to 37° C.-100° C. over 1-20 minutes.

In some embodiments, the reaction mixture is heated over 1-15 minutes.

In some embodiments, the reaction mixture is heated over 1-10 minutes.

In some embodiments, the reaction mixture is heated over 1-5 minutes.

In some embodiments, the reaction mixture is heated over 5 minutes.

In some embodiments, the reaction mixture is heated to 37° C.-85° C.

In some embodiments, the reaction mixture is heated to 37° C.-75° C.

In some embodiments, the reaction mixture is heated to 37° C.-65° C.

In some embodiments, the reaction mixture is heated to 37° C.-55° C.

In some embodiments, the reaction mixture is heated to 37° C.-45° C.

The person skilled in the art will appreciate that the temperature to which the reaction mixture is heated so enact release of complementary oligonucleotide regions depends on the length of said regions.

In some embodiments, release is achieved through the cleavage of one or more oligonucleotide sequences. This cleavage can be achieved by any of the means previously, or subsequently, described or by any of the means known to the person skilled in the art.

In some embodiments, oligonucleotide sequences are cleaved chemically.

In some embodiments, oligonucleotide sequences are cleaved enzymatically.

In some embodiments, oligonucleotide sequences are cleaved by a restriction enzyme.

In some embodiments, oligonucleotide sequences are cleaved by epigenetic modification sensitive or dependent restriction enzymes.

In some embodiments, oligonucleotide sequences are cleaved by methylation sensitive or dependent restriction enzymes.

In some embodiments, oligonucleotide sequences are cleaved by hydroxymethylation sensitive or dependent restriction enzymes.

In some embodiments, prior to, or after, enrichment of variant or wild-type sequences, sequences are enzymatically or chemically converted to allow detection of their methylation status. The person skilled in the art will appreciate that the term 'enrichment' refers to the selective isolation of target sequences from a mixture of target and non-target sequences, as described previously or subsequently.

In some embodiments, the restriction enzymes are endonucleases.

In some embodiments, oligonucleotide sequences are cleaved by a flap endonuclease.

In some embodiments, oligonucleotide sequences comprise a photocleavable linker and oligonucleotide sequences are released from the solid support by cleavage of this linker.

In some embodiments, oligonucleotide sequences are released from the solid support by cleavage of this linker.

In some embodiments, the digestion continues until $A_0$ lacks sufficient complementarity with the sequence for the pyrophosphorolysing enzyme to bind or for the pyrophosphorolysing reaction to continue. This typically occurs when there are between 6 and 20 complementary nucleotides remaining between the sequence and probe. In some embodiments, this occurs when there are between 6 and 40 complementary nucleotides remaining.

Without being constrained by theory, there are a number of different ways in which the pyrophosphorolysis reaction may be stopped, in addition to those described previously or elsewhere.

If the pyrophosphorolysis enzyme has the ability to 'read ahead', the digestion may stop 3' of a mismatch or base modification. Such activity has been observed in archaeal DNA polymerases.

In some embodiments, the pyrophosphorolysis reaction may stop due to the presence of a modification in the backbone of $A_0$.

This modification may be a modified base. The base may be resistant to pyrophosphorolysis.

This modification may be a chemical backbone modification.

In some embodiments, the pyrophosphorolysis reaction may stop due to the presence of mismatch in $A_0$. The location of this mismatch may be purposefully designed such that digestion halts at this defined point.

In some embodiments, the temperature of the reaction mixture may be increased to heat-inactivate the pyrophosphorolysis enzyme. In some embodiments, the temperature is increased to cause the probe-target duplex to melt apart.

In some embodiments, any reagent that could cause the inactivation of the pyrophosphorolysis enzyme may be added to the reaction mixture.

In some embodiments, the pH concentration may be modified to inactivate pyrophosphorolysis enzyme.

In some embodiments, the salt concentration may be modified to inactivate pyrophosphorolysis enzyme.

In some embodiments, the detergent concentration may be modified to inactivate pyrophosphorolysis enzyme.

In some embodiments, the ion concentration may be modified to inactivate pyrophosphorolysis enzyme.

The person skilled in the art will appreciate that there are numerous further ways in which an enzyme catalysed reaction may be brought to a halt and the above disclosure is not intended to limit the scope of the invention.

Suitably, pyrophosphorolysis is carried out in the reaction medium at a temperature in the range 20 to 90° C. in the presence of at least a polymerase exhibiting pyrophosphorolysis activity and a source of pyrophosphate ion. Further information about the pyrophosphorolysis reaction as applied to the digestion of polynucleotides can be found for example in J. Biol. Chem. 244 (1969) pp. 3019-3028.

In some embodiments, the pyrophosphorolysis step is driven by the presence of a source of excess polypyrophosphate, suitable sources including those compounds containing 3 or more phosphorous atoms.

In some embodiments, the pyrophosphorolysis step is driven by the presence of a source of excess modified pyrophosphate. Suitable modified pyrophosphates include those with other atoms or groups substituted in place of the bridging oxygen, or pyrophosphate (or poly-pyrophosphate) with substitutions or modifying groups on the other oxygens. The person skilled in the art will understand that there are many such examples of modified pyrophosphate which would be suitable for use in the current invention, a non-limiting selection of which are:

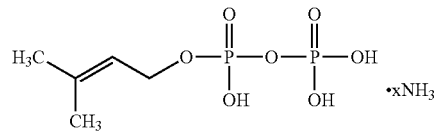

Y,Y-Dimethylallyl pyrophosphate ammonium salt

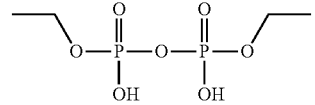

Diethyl acid pyrophosphate

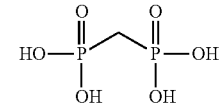

PCP

Tripolyphosphoric Acid (PPPi)

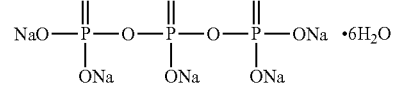

Pentasodium tripolyphosphate hexahydrate

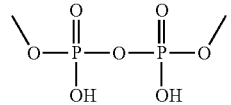

Dimethyl acid pyrophosphate

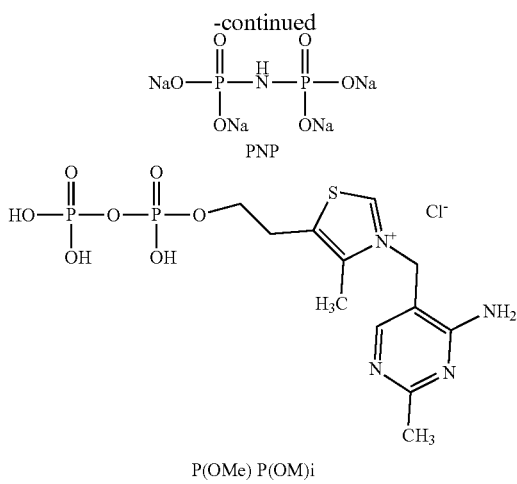

PNP

P(OMe) P(OM)i

In one preferred embodiment, the source of pyrophosphate ion is PNP, PCP or Tripolyphoshoric Acid (PPPi).

Further, but not limiting, examples of sources of pyrophosphate ion for use in the pyrophosphorolysis step may be found in WO2014/165210 and WO00/49180.

In some embodiments, the source of excess modified pyrophosphate can be represented as Y—H wherein Y corresponds to the general formula (X—O)$_2$P(=B)—(Z—P(=B)(O—X))$_n$— wherein n is an integer from 1 to 4; each Z— is selected independently from —O—, —NH— or —CH$_2$—; each B is independently either O or S; the X groups are independently selected from —H, —Na, —K, alkyl, alkenyl, or a heterocyclic group with the proviso that when both Z and B correspond to —O— and when n is 1 at least one X group is not H.

In some embodiments, Y corresponds to the general formula (X—O)$_2$P(=B)—(Z—P(=B)(O—X))$_n$— wherein n is 1, 2, 3 or 4. In another embodiment, the Y group corresponds to the general formula (X—O)$_2$P(=O)—Z—P(=O)(O—H)— wherein one of the X groups is —H. In yet another preferred embodiment, Y corresponds to the general formula (X—O)$_2$P(=O)—Z—P(=O)(O—X)— wherein at least one of the X groups is selected from methyl, ethyl, allyl or dimethylallyl.

In an alternative embodiment, Y corresponds to either of the general formulae (H—O)$_2$P(=O)—Z—P(=O)(O—H)— wherein Z is either —NH— or —CH$_2$— or (X—O)$_2$P(=O)—Z—P(=O)(O—X)— wherein the X groups are all either —Na or —K and Z is either —NH— or —CH$_2$—.

In another embodiment, Y corresponds to the general formula (H—O)$_2$P(=B)—O—P(=B)(O—H)— wherein each B group is independently either O or S, with at least one being S.

Specific examples of preferred embodiments of Y include those of the formula (X1-O)(HO)P(=O)—Z—P(=O)(O—X2) wherein Z is O, NH or CH$_2$ and (a) X1 is γ,γ-dimethylallyl, and X2 is —H; or (b) X1 and X2 are both methyl; or (c) X1 and X2 are both ethyl; or (d) X1 is methyl and X2 is ethyl or vice versa.

The person skilled in the art will appreciate that there are multiple techniques which may be used to fragment DNA. Such methods include sonication, needle shear, nebulisation, point-sink shearing, passage through a pressure cell (French press) and enzymatic methods.

In some embodiments, fragmentation is achieved by sonication. In some embodiments, The Bioruptor® (Denville, N.J.) device may be used.

In some embodiments, fragmentation is achieved by acoustic shearing. In some embodiments, the Covaris® instrument (Woburn, Mass.) may be used.

In some embodiments, fragmentation is achieved by nebulisation. Nebulization forces DNA through a small hole in a nebulizer unit, which results in the formation of a fine mist that is collected. Fragment size is determined by the pressure of the gas used to push the DNA through the nebulizer, the speed at which the DNA solution passes through the hole, the viscosity of the solution, and the temperature.

In some embodiments, fragmentation is achieved by hydrodynamic shear. In some embodiments, The Hydroshear from Digilab (Marlborough, Mass.) may be used.

In some embodiments, fragmentation is achieved by point-sink shearing.

In some embodiments, fragmentation is achieved by needle shearing.

In some embodiments, fragmentation is achieved via use of a French press.

In some embodiments, fragmentation is achieved by enzymatic fragmentation.

In some embodiments, fragmentation is achieved by restriction endonuclease digestion.

In some embodiments, fragmentation is transposome mediated fragmentation.

In some embodiments, fragmentation is achieved by Cas9.

In some embodiments, fragmentation is achieved by Cas9, as described in U.S. Ser. No. 10/577,644, herein incorporated by reference in its entirety.

In some embodiments, one or more different fragmentation techniques may be used.

In some embodiments, one or more of the same or different fragmentation techniques may be used at one or more different points of the method.

In some embodiments, fragmentation and adaptor tagging of sequences occurs at the same time or in the same step of the method. One such example is Nextera DNA Library Prep Kit by Illumina.

The person skilled in the art will appreciate that there are multiple techniques which may be used to prepare adaptor tagged sequences/libraries.

In some embodiments, following fragmentation, the ends of nucleic acids may be polished and A-tailed prior to ligation to one or more adaptors.

In some embodiments, following fragmentation, the ends of nucleic acids may be polished and ligated to adaptors in a blunt-end ligation reaction.

In some embodiments, following fragmentation, adaptors are ligated to single-stranded DNA.

In some embodiments, following fragmentation, a terminal transferase enzyme is used to add non-templated bases to the 3' end of fragments, providing a site for priming to make fragments double-stranded.

In some embodiments, topoisomerase may be used in lieu of a DNA ligase.

In some embodiments, TOPO cloning may be used to add adaptors to fragmented DNA.

In some embodiments, following fragmentation, transposases can be used to add adaptor sequences to nucleic acids.

In some embodiments, following fragmentation, standard transposons can be used but then modified to create a Y-shaped adaptor using oligonucleotide replacement.

In some embodiments, wherein the sample is an adaptor tagged library, blocking oligonucleotides are used to prevent cross-hybridisation of library molecules (so called 'daisy chaining').

In some embodiments, blocking oligonucleotides are resistant to pyrophosphorolysis. This resistance may be as previously or subsequently described.

If the library is adaptor tagged, and has been PCR amplified, then double-stranded molecules have strands 5'-adaptor1-insert-adaptor2'-3' and 5'-adaptor2-insert-adaptor1'-3'. During hybridisation, the 5'-adaptor1-3' sequence on one strand could hybridise to a 5'-adaptor1'-3' sequence on a second strand. Similarly, the 5'-adaptor2'-3' sequence on one strand can hybridise to a 5'-adaptor2-3' sequence on a second strand. These hybridisation events can chain together, generating a so-called 'daisy chain' of molecules, including both target and non-target molecules.

In the context of the pyrophosphorolysis reaction, hybridisation of 5'-adaptor1-3' and 5'-adaptor1'-3' or hybridisation of 5'-adaptor2-3' and 5'-adaptor2'-3' both generate a 3' end that could be subject to pyrophosphorolysis.

In this context, pyrophosphorolysis could remove bases from the 3' of a target molecule, preventing its amplification during PCR. Blocking oligonucleotides are typically used in hybridisation capture to mitigate against daisy-chaining.

In the context of the molecules described above, these could be sequence complementary to adaptor1' and sequence complementary to adaptor2'. The blocking oligonucleotides can be protected from pyrophosphorolysis by addition of 3' phosphorothioate bonds or by ensuring that the 3' of the adaptor tagged molecules is non-complementary to the blocking oligonucleotide. In another example, alpha-thio-dNTPs that introduce phosphorothioate bonds that inhibit pyrophosphorolysis could be included in a PCR, or primer extension reaction, prior to pyrophosphorolysis.

There is thus provided an embodiment wherein blocking oligonucleotides as previously or subsequently described are used in the method. In some embodiments, the sample comprises one or more blocking oligonucleotides.

In some embodiments, the first reaction mixture comprises one or more blocking oligonucleotides.

In some embodiments, the second reaction mixture comprises one or more blocking oligonucleotides.

In some embodiments, one or more blocking oligonucleotides are introduced to the first reaction mixture prior to step (b).

In some embodiments, the sequencing of the method is Maxam-Gilbert sequencing.

In some embodiments, the sequencing of the method is Sanger sequencing.

In some embodiments, the sequencing of the method is shotgun sequencing.

In some embodiments, the sequencing of the method is single-molecule real-time sequencing.

In some embodiments, the sequencing of the method is ion semiconductor sequencing.

In some embodiments, the sequencing of the method is pyrosequencing.

In some embodiments, the sequencing of the method is sequencing by synthesis.

In some embodiments, the sequencing of the method is combinatorial probe anchor synthesis (cPAS).

In some embodiments, the sequencing of the method is sequencing by ligation.

In some embodiments, the sequencing of the method is nanopore sequencing.

In some embodiments, the sequencing of the method is GenapSys sequencing.

In some embodiments, the sequencing is Next Generation Sequencing (NGS).

In some embodiments, there is provided a method for screening a patient comprising the use of any previously or subsequently described embodiment of the method to detect the presence or absence of one or more specific nucleic acid sequences in a sample derived from a patient.

The person skilled in the art will appreciate that such a screening will be useful for monitoring a transplant recipient patient.

The person skilled in the art will appreciate that such a screening will be useful for monitoring a patient receiving treatment for one or more conditions, the treatment status of which can be ascertained by the levels of one or more nucleic acid sequences in a patient sample.

For example, the treatment status of patients receiving treatment for one or more cancers can be ascertained by the levels of one or more nucleic acid sequences in their blood and/or the presence and/or absence of one or more specific variants. A high level of circulating tumour nucleic acid sequences and/or the presence and/or absence of one or more specific variants, can be used to deduce whether or not a particular treatment is having the desired effect. There is thus provided a method for monitoring the success, or not, of a particular treatment wherein such success can be inferred by the presence or absence of specific nucleic acid sequences and/or their respective levels in a sample derived from a patient.

In some embodiments, there is provided a method of monitoring a patient in remission to detect any recurrence of disease.

In some embodiments, there is provided a method of screen nominally healthy people to detect the presence of one or more disease states including, but not limited to, cancer.

in some embodiments, there is provided a method of detecting the presence and/or absence of one or more genetic markers in a patient diagnosed with one or more disease states and using the presence and/or absence of one or more markers to determine which treatment they should receive.

In some embodiments, there is provided a method for the diagnosis and/or monitoring of one or more cancers in a patient comprising the use of any previously or subsequently described embodiment of the method to detect the presence or absence of one or more specific nucleic acid sequences in a sample derived from a patient.

The person skilled in the art will appreciate that the one or more specific nucleic acid sequences may be specific to an individual (identified from a tissue biopsy or surgical resection, for example, by a method of identification such as sequencing) and that in such cases an individual patient specific panel may be used.

The person skilled in the art will further appreciate that in some embodiments, a panel will cover known hotspot regions of the human genome, those that are recurrently mutated in a given cancer type.

In some embodiments, there is provided a method for non-invasive prenatal testing (NIPT) comprising the use of any previously or subsequently described embodiments of the method to detect the presence or absence of one or more specific nucleic acid sequences in a sample derived from a patient, wherein the patient is a pregnant patient. In some embodiments, the sample is the plasma and or serum of the blood of a pregnant patient. In some embodiments, methods provided herein are employed to enrich and/or quantify a fetal fraction of a sample using a panel of common SNPs associated with such samples.

In some embodiments, there is provided a method of treating a patient comprising the steps of:
Performing any of the previously or subsequently described embodiments of the invention to detect the absence or presence of one or more specific nucleic acid sequences in a sample derived from a patient;
Making one or more treatment decisions based on the presence or absence of said sequences.

In some embodiments, the treatment decision is the initiation of a particular treatment.

In some embodiments, the treatment decision is the cessation of a particular treatment.

In some embodiments, the treatment decision is an increase in the dose of a particular treatment.

In some embodiments, the treatment decision is a decrease in the dose of a particular treatment.

In some embodiments, the treatment decision is an increase in the frequency of administration of a particular treatment.

In some embodiments, the treatment decision is a decrease in the frequency of administration of a particular treatment.

In some embodiments, the treatment decision is the addition of an additional drug to an existing treatment regimen.

In some embodiments, the treatment decision is the removal of a drug from an existing treatment regimen.

In an aspect of the present invention, there is provided a device for performing the methods of the current invention.

In some embodiments, there is provided a device for performing steps (a)-(c) of the method.

In some embodiments, there is provided a device for performing steps (a)-(b) of the method. In an aspect of the present invention, there is provided a kit comprising one or more oligonucleotides, enzymes, reagents or components as previously or subsequently described in one or more embodiments.

In some embodiments, there is provided a kit comprising:
One or more oligonucleotides $A_0$, wherein $A_0$ comprises:
 a sequence (e.g., at a 3' end of $A_0$ or elsewhere) which is complementary to (e.g., perfectly complementary to) a known first sequence but less complementary to (e.g., imperfectly complementary to) a known second sequence;
One or more pyrophosphorolysing enzymes; and
One or more sources of pyrophosphate ions.

In some embodiments, the kit further comprises one or more solid supports. These solid supports may be as previously or subsequently described.

In some embodiments, the kit further comprises one or more buffers. These buffers may be as previously or subsequently described.

In some embodiments, the kit further comprises one or more crowing agents (e.g., polyethylene glycol (PEG), poly(vinyl alcohol) (PVA), dextran sulphate, etc.).

In some embodiments, the kit further comprises one or more detergents (e.g., sodium dodecyl sulfate (SDS), TWEEN20, etc.).

In some embodiments, the kit further comprises one or more solvents (e.g., formamide, ethylene carbonate, etc.).

In some embodiments, the kit further comprises a phosphohydrolase (e.g. Apyrase).

In some embodiments, the kit further comprises a pyrophosphatase (e.g. Thermostable Inorganic Pyrophosphatase (TIPP) (New England Biolabs)).

In some embodiments, the one or more buffers may include additives which hybridise to repetitive sequences. In some embodiments, the one or more buffers may include C0t-1 DNA, salmon sperm DNA, oligonucleotides that block ribosomal RNA, and the like.

In some embodiments, $A_0$ further comprises a 5' tail region which is not complementary to either a known first or known second sequence. $A_0$ may be as previously or subsequently described.

In some embodiments, $A_0$ further comprises a capture moiety.

In some embodiments, the kit further comprises one or more capture oligonucleotides ($C_0$), as previously or subsequently described.

In some embodiments, the kit further comprises one or more capture oligonucleotide $C_0$ which comprises a capture moiety and wherein a 5' tail region of $A_0$ is complementary to a region of $C_0$.

In some embodiments, the capture moiety is biotin and the solid support comprises streptavidin.

In some embodiments, the solid support comprises a capture oligonucleotide $C_0$ and wherein a 5' tail region of $A_0$ is complementary to a region of $C_0$.

In some embodiments, the solid support is a bead.

In some embodiments, the bead is a magnetic or paramagnetic bead.

In some embodiments, the kit further comprises one or more epigenetic modification sensitive or dependent restriction enzymes.

In some embodiments, the kit further comprises one or more transposomes.

In some embodiments, the kit further comprises Cas9.

In some embodiments, the kit further one or more transposases.

In some embodiments, the kit further comprises one or more ligases.

In some embodiments, the kit further comprises one or more metal ions.

In some embodiments, the kit further comprises one or more blocking oligonucleotides.

In some embodiments, the one or more blocking oligonucleotides are resistant to pyrophosphorolysis.

In some embodiments, the kit further comprises isothermal amplification reagents.

In some embodiments, the kit further comprises Polymerase Chain Reaction (PCR) reagents (e.g., thermostable DNA polymerases, primers, dNTPs, buffer solution).

In some embodiments, the kit further comprises sequencing reagents.

In some embodiments, the kit further comprises Next Generation Sequencing (NGS) reagents (e.g., polymerases, dNTPs, buffer solution).

In some embodiments, the kit further comprises a DNA library preparation kit (e.g., containing, as desired, polymerases, ligases, adapters, dNTPs, buffer solutions).

In some embodiments, the kit further comprises one or more molecular probes.

In some embodiments, the kit further comprises one or more molecular probes which are fluorescently labelled.

In some embodiments, a region of $A_0$ (e.g., the 3' end of) is more complementary to (e.g., perfectly complementary to) a wild type sequence of the human genome and less complementary to (e.g., imperfectly complementary to) a mutant allele of said wild type sequence.

In some embodiments, a region of $A_0$ (e.g., the 3' end of) is less complementary to (e.g., imperfectly complementary to) a wild type sequence of the human genome and more complementary to (e.g., perfectly complementary to) a mutant allele of said wild type sequence.

In some embodiments, the kit further comprises one or more components for the transcription of RNA into cDNA.

In some embodiments, the kit further comprises one or more kits for the preparation of adaptor tagged libraries for sequencing, as previously or subsequently described or otherwise known to the person skilled in the art.

In some embodiments, the kit further comprises one or more components for the fragmentation of nucleic acids, as previously or subsequently described or otherwise known to the person skilled in the art.

In some embodiments, the kit further comprises one or more devices for the physical fragmentation of nucleic acids, as previously or subsequently described or otherwise known to the person skilled in the art.

In some embodiments, the kit alternatively further comprises one or more components for the enzymatic fragmentation of nucleic acids, as previously or subsequently described or otherwise known to the person skilled in the art.

In some embodiments, the kit further comprises one or more components for the physical fragmentation of nucleic acids and one or more components for the enzymatic fragmentation of nucleic acids.

In some embodiments, there is provided a kit comprising multiple $A_O$, as previously or subsequently described.

In some embodiments, there is provided a kit comprising 1-1,000,000 individual $A_O$ probes, each of which have sequences (e.g., 3' ends) which are perfectly complementary to an individual mutation, wherein the same sequences (e.g., at 3' ends or elsewhere) are imperfectly complementary to the wild type sequence of said mutation. In some embodiments, there is provided a kit comprising 1-100,000 individual $A_O$ probes. In some embodiments, there is provided a kit comprising 1-10,000 individual $A_O$ probes. In some embodiments, there is provided a kit comprising 1-1,000 individual $A_O$ probes.

In some embodiments, there is provided a kit comprising 1-1,000,000 individual $A_O$ probes, each of which have sequences (e.g., 3' ends or elsewhere) which are imperfectly complementary to an individual mutation, wherein the same sequences (e.g., at 3' ends or elsewhere) are perfectly complementary to the wild type sequence of said mutation. In some embodiments, there is provided a kit comprising 1-100,000 individual $A_O$ probes. In some embodiments, there is provided a kit comprising 1-10,000 individual $A_O$ probes. In some embodiments, there is provided a kit comprising 1-1,000 individual $A_O$ probes.

In some embodiments, there is provided a kit comprising multiple capture oligonucleotides ($C_O$) as previously or subsequently described.

In some embodiments, there is provided a kit comprising multiple solid supports as previously or subsequently described.

In some embodiments, there is provided a panel comprising multiple $A_O$ which have sequences (e.g., at their 3' ends) which are perfectly complementary to known sequences.

In some embodiments, there is provided a panel comprising multiple $A_O$ which have sequences (e.g., at their 3' ends) which are imperfectly complementary to known sequences.

In some embodiments, there is provided a panel comprising multiple $A_O$ which have sequences (e.g., at their 3' ends) which are perfectly complementary to known variants in a given cancer type or range of cancer types.

In some embodiments, there is provided a panel comprising multiple $A_O$ which have sequences (e.g., at their 3' ends) which are imperfectly complementary to known variants in a given cancer type or range of cancer types, wherein the sequences (e.g., at their 3' ends) are perfectly complementary to the wild-type sequences.

In some embodiments, there is provided a panel comprising multiple $A_O$ some of which have sequences (e.g., at their 3' ends) which are perfectly complementary to known variants in a given cancer type or range of cancer types whilst others are imperfectly complementary.

In some embodiments, the panel further comprises one or more capture oligonucleotides ($C_O$) as previously or subsequently described.

In some embodiments, the panel further comprises one or more blocking oligonucleotides as previously or subsequently described.

A polymorphism (e.g., mutation) may be selected from any polymorphism (e.g., mutation) previously, or subsequently, described or known. The person skilled in the art will thus appreciate that within the scope of the invention are included panels which may be useful in the detection of one or more polymorphisms (e.g., mutations) to any of the proto-oncogenes, oncogenes, or genetic markers for one or more disease states previously, or subsequently, described or known.

The person skilled in the art will further appreciate that within the scope of the invention are included panels which may be useful in the detection of more variants that could be used in determining the presence, or absence, of genetic markers for one or more disease states or that are specific for a given patient, tissue, or cell, for example for tumor-informed monitoring.

The person skilled in the art will further appreciate that within the scope of the invention are included panels which may be useful in the detection of one or more variants which are as yet unknown but which nonetheless could be used in determining the presence, or absence, or one or more disease states. For example, there are known mutational signatures for many different cancer types, these are preferential modes of mutagenesis such as excess C>T at CpG dinucleotides. Panels may comprise probes that are designed to detect these types of events occurring.

In some embodiments, the panel comprises 1-1,000,000 individual probe molecules, each of which has a sequence (e.g., at their 3' end) which may be complementary to a specific target region including a target mutation.

In some embodiments, the panel comprises 10,000-1,000,000 individual probe molecules, each of which has a sequence (e.g., at their 3' end) which may be complementary to a specific target region including a target mutation.

In some embodiments, the panel comprises 100,000-1,000,000 individual probe molecules, each of which has a sequence (e.g., at their 3' end) which may be complementary to a specific target region including a target mutation.

In some embodiments, the panel comprises 200,000-1,000,000 individual probe molecules, each of which has a sequence (e.g., at their 3' end) which may be complementary to a specific target region including a target mutation.

In some embodiments, the panel comprises 10,000-100,000 individual probe molecules, each of which has a sequence (e.g., at their 3' end) which may be complementary to a specific target region including a target mutation.

In some embodiments, the panel comprises 1,000-100,000 individual probe molecules, each of which has a sequence (e.g., at their 3' end) which may be complementary to a specific target region including a target mutation.

In some embodiments, the panel comprises 1,000-10,000 individual probe molecules, each of which has a sequence (e.g., at their 3' end) which may be complementary to a specific target region including a target mutation.

In some embodiments, the panel comprises 500-10,000 individual probe molecules, each of which has a sequence (e.g., at their 3' end) which may be complementary to a specific target region including a target mutation.

In some embodiments, the panel comprises 500-1,000 individual probe molecules, each of which has a sequence (e.g., at their 3' end) which may be complementary to a specific target region including a target mutation.

In some embodiments, the panel comprises 5-500 individual probe molecules, each complementary to a specific target mutation. In some embodiments, the panel comprises 5-400 individual probe molecules, each complementary to a specific target mutation. In some embodiments, the panel comprises 5-300 individual probe molecules, each complementary to a specific target mutation. In some embodiments, the panel comprises 5-200 individual probe molecules, each complementary to a specific target mutation. In some embodiments, the panel comprises 5-100 individual probe molecules, each complementary to a specific target mutation. In some embodiments, the panel comprises 5-50 individual probe molecules, each complementary to a specific target mutation.

In some embodiments, there may be a plurality of probe molecules specific to the same mutation. In some embodiments, there may be only one probe molecule specific to each mutation of the panel.

In some embodiments, there is provided a panel, wherein the panel comprises a plurality of probe molecules wherein one or more probes are complementary to an EGFR mutation, one or more probes are complementary to a KRAS mutation, one or more probes are complementary to a ERBB2/HER2 mutation, one or more probes are complementary to a EML4-ALK mutation, one or more probes are complementary to a ROS1 mutation, one or more probes are complementary to a RET mutation and one or more probes are complementary to a MET mutation.

In some embodiments, there is provided a panel, wherein the panel comprises a plurality of probe molecules wherein one or more probes may be complementary to an EGFR mutation, one or more probes may be complementary to a KRAS mutation, one or more probes may be complementary to a ERBB2/HER2 mutation, one or more probes may be complementary to a EML4-ALK mutation, one or more probes may be complementary to a ROS1 mutation, one or more probes may be complementary to a RET mutation and one or more probes may be complementary to a MET mutation.

In some embodiments, there is provided a panel of probes selective for one or more EGFR, KRAS, BRAF, ERBB2/HER2, EML4-ALK, ROS1, RET, MET mutations.

In some embodiments, there is provided a panel of probe molecules selective for EGFR mutations.

In some embodiments, there is provided a panel of probe molecules selective for KRAS mutations.

In some embodiments, there is provided a panel of probe molecules selective for BRAF mutations.

In some embodiments, there is provided a panel of probe molecules selective for ERBB2/HER2 mutations.

In some embodiments, there is provided a panel of probe molecules selective for EML4-ALK mutations.

In some embodiments, there is provided a panel of probe molecules selective for ROS1 mutations.

In some embodiments, there is provided a panel of probe molecules selective for RET mutations.

In some embodiments, there is provided a panel of probe molecules selective for NTRK mutations.

In some embodiments, there is provided a panel of probe molecules selective for ROS1 mutations.

In some embodiments, there is provided a panel of probe molecules selective for MET exon 14 mutations.

In some embodiments, there is provided a panel comprising a plurality of probe molecules selective for one or more coding sequences (CDSs).

In some embodiments, there is provided a method of detecting one or more mutations using one or more of the previously described panels.

In some embodiments, there is provided a method of detecting the presence or absence of one or one or more mutations using one or more of the previously described panels.

In some embodiments, there is provided a kit comprising a panel, which may be as previously or subsequently described, in combination with one or more reagents, which may be as previously or subsequently described.

The person skilled in the art will appreciate that the terms 'DNA' and 'nucleic acid' are used interchangeably within this application. Therefore, disclosure of embodiments which refer to 'DNA' can be understood to encompass and disclose embodiments wherein 'DNA' is replaced with 'nucleic acid'. The person skilled in the art will appreciate, thereof, that embodiments which refer to 'DNA' can be understood to encompass and disclose embodiments wherein 'DNA' is replaced with 'RNA'.

It will further be appreciated by those skilled in the art that although the invention has been described by way of example with reference to several embodiments, it is not limited to the disclosed embodiments and that alternative embodiments could be constructed without departing from the scope of the invention as defined in the appended claims.

As used herein, "magnetic microparticles" are magnetically responsive microparticles which are attracted by a magnetic field. The magnetic microparticles which may be used in the methods of the present invention comprise a magnetic metal oxide core, which is generally surrounded by a polymer coat which creates a surface that can bind to DNA, RNA, or PNA. The magnetic metal oxide core is preferably iron oxide, wherein iron is a mixture of Fe' and Fe'. The preferred Fe'/Fe' ratio is preferably 2/1, but can vary from about 0.5/1 to about 4/1.

Bioinformatics approaches are used to analyse sequencing data. In some embodiments, the presence or absence of specific variants is called. In other embodiments, data from multiple variants are combined to derive a probabilistic estimate for the presence or absence of tumor DNA.

For example, Illumina sequencing data analysis includes conversion and demultiplexing of BCL files into FASTQ format using tools such as bcl2fastq. In some embodiments, sequencing reads include molecular identifiers. In this case, molecular identifiers can be extracted from sequencing reads, appended to FASTQ headers, and the sequencing reads clipped. In some embodiments, barcodes with non-canonical bases (not A, C, G or T) can be filtered. The resulting reads can then be aligned using a tool such as bwa mem, using the —C option to append barcode sequences to alignments. Alignments can then be sorted by coordinate, duplicate reads marked, and reads annotated with read coordinate, mate coordinate and optical duplicate auxiliary tags using biobambam2 bamsormadup and bammarkduplicatesopt. Reads can be filtered if they are not marked as proper-pairs or were marked as optical duplicate, supplementary, QC fail, unmapped or secondary alignments. Each read can then be marked with an auxiliary tag comprised of reference name, sorted read and mate fragmentation breakpoints, forward and reverse read barcodes, and read strand.

In some embodiments, the sequencing data is analysed using a variant calling algorithm that does not use auxiliary tag data. In this case, analysis of sequencing data compares the probability of observing data under two models. The first is a null model specifying the distribution of sequencing artifacts. The second is a model allowing for true variants. In this case, a variant is called if the probability under the alternative model exceeds that of the null model. In some embodiments, a panel of pre-characterised samples can help to model the error distribution for (first model).

In some embodiments, auxiliary tags can be used to identify reads that likely derive from the same input molecule, and/or same strand of the same input molecule. In some embodiments, consensus base quality scores can be derived from reads that share the same auxiliary tag.

In some embodiments, variants are identified using an artificial intelligence algorithm such as convolutional neural networks.

In some embodiments, sequencing data can be further filtered to remove artefacts. Example filters include the number of mismatches present on a given sequencing read; the alignment score and next best alignment score; base quality scores or consensus base quality scores; the minimum number of reads covering a given variant site; the position of the variant within the sequencing read; whether reads are 5' clipped; whether reads are improper pairs; whether reads contain indels; and the variant allele fraction of a given variant. In some embodiments, regions of the genome that include common SNPs, or are prone to alignment artefacts are filtered. There are many other filters known to the person skilled in the art.

In some embodiments a control sample is sequenced to filter out variants. For example, DNA from buccal epithelial, or other tissue sources, could be sequenced to remove germline variants. In another embodiment, buffy coat or leukocyte DNA can be sequenced to filter out somatic mutations that derive from clonal haematopoiesis.

The compositions, methods, and kits of the invention find use in a diverse range of applications and setting. In some embodiments, they find use in any methodology where a sequence is desired to be detected in a sample. In some embodiments, they find use in any methodology where there is a desire to detect a minority (e.g., rare) sequence in a complicated sample. In addition to the exemplary uses described above, a number of additional illustrative uses are provided below.

In some embodiments, the compositions, methods, and kits find use in the analysis and treatment of infectious diseases. The technology is of particular value for detection of low frequency mutations that may be present in a sample. For example, the technology finds use for the detection of low frequency mutations associated with treatment resistant (e.g., antibiotic resistant, anti-viral resistant, etc.) infectious diseases (e.g., HIV, tuberculosis, etc.). The technology further finds use in selective pulldown of bacterial or viral DNA or RNA for sequencing.

As noted above, the technology is particularly well suited to the analysis and/or enrichment of analytes in complicated samples. One area of growing research and clinical interest is microbiome analysis where the technology finds use to provide much higher specificity selection of desired bacterial DNA for sequencing or other analysis.

The technology also finds use in high throughput analysis of many different samples as well as multiplex analysis.

These benefits find use in a wide variety of genotyping applications, including forensic analysis, paternity/maternity testing, disease analysis (e.g., cancer, infectious disease), drug susceptibility testing, agriculture and food testing (e.g., to assist with selective breeding, to identify trace contaminants, etc.).

The technology finds use in synthetic nucleic acid (e.g., DNA) error correction. Synthetic nucleic acid is used in research, diagnostic, and clinical indications. It is often important to avoid or minimizing use of nucleic acid molecules having unintended or undesired sequences. The technology finds use in identification and isolation of desired molecules from undesired molecules.

Nucleic acid editing is emerging as an important process in research, synthetic biology, and clinical applications. For example, CRISPR/CAS editing of nucleic acids, and related processes, are emerging as important processes. Many of these editing techniques result in a mixed populations of molecules that include intended edited products, unedited products, and unintended edited products. The technology provided herein facilitates identification, selection, and isolation if intended edited products.

The technology also finds use in environmental monitoring. In addition to agricultural uses, the technology is particularly well suited to the analysis of environmental samples that may contain trace amounts of an analyte of interest. Such samples include, but are not limited to, analysis of native and invasive species of organisms, early detection of invasive species, air and water contamination, and ancient DNA analysis. Sample types include, but are not limited to, soil, water, snow, feces, mucus, gametes, shed skin, carcasses, hair, and air.

The technology finds use in the isolation of a desired subset of nucleic acid from a particular sample from other subsets. For example, the technology finds use in the isolation and analysis of chloroplast and mitochondrial genomes.

The technology finds use in cell line screening for engineered and natural cells. Such cell lines include, but are not limited to, cell cultures (primary and immortalized), stems cells (embryonic, induced pluripotent, de-differentiated, etc.), differentiated cells intended for cell therapies, ex vivo modified cells for research or clinical applications (e.g., CAR T cells), and genetically engineered cells.

The technology finds use to removed damaged or other undesired nucleic acid away from undamaged or desired nucleic acid. For example, the technology may be used to remove damaged DNA from a sample prior to methylation analysis.

The technology finds use in pre-implantation screening of cells (e.g., embryos, eggs, sperm), liposomes, exosomes, nucleic acid vectors (e.g., gene therapy vector), and the like prior to there administration to a subject.

The technology finds use in drug toxicity screening. The technology is particularly well suited to the identification of DNA damage, generation of mutations, methylation changes, and the like that may be associated with the use of particular drugs.

The technology finds use in fragmentomic analysis of nucleic acids. For example, probes may be used that reside over or are aligned with a breakpoint that associates a particular sequence with relevant correlated information (e.g., tissue of origin, association with diseases such as cancer, etc.).

The technology may be used in any application where nucleic acid complexity reduction is desired. For example, the technology may be used for whole genome complexity reduction. In some such embodiments, a restriction enzyme digestion or other nucleic acid fragmenting process is used followed by the step of pulling out only cleaved molecules using probes that match known end sequences.

The technology finds use in assessing microsatellite instability (MSI). Target nucleic acid molecules that differ in the presence of, number or, or nature of repeated nucleotides (e.g., GT/CA repeats) are enriched and/or identified in a sample. MSI is associated with a number of diseases and conditions including, but not limited to, colon cancer, gastric cancer, endometrium cancer, ovarian cancer, hepatobiliary tract cancer, urinary tract caner, brain cancer, and skin cancers.

The technology also finds use in assessing tumor mutational burden (TMB). TMB has emerged as a predictive biomarker for immune checkpoint therapy, among other uses. Currently, next-generation, whole-exome sequencing is employed to assess TMB or a gene panel that provides sequences of a subset of genes is assessed. Use of the technology provided herein allows for TMB assessments that are more sensitive and significantly less costly and burdensome.

The technology finds use in haplotying. Genomic information reported as haplotypes rather than genotypes is increasingly important for personalized medicine, as well as a wide variety of research applications. Haplotypes, that are more specific than less complex variants such as single nucleotide variants, also have applications in prognostics and diagnostics, in the analysis of tumors, and in typing tissue for transplantation. Presently, sequencing is the most common form of molecular haplotyping. The error rate of sequencing technologies presents a barrier to obtaining accurate information. The technology provided herein allows for efficient and highly accurate haplotying.

The ability of the technology to enrich for any desired sequence or interest allow the technology to enhance existing nucleic acid methodologies. For example, many nucleic acid sequencing approaches struggle when there are repetitive sequence regions in a target nucleic acid. The technology provided herein permits removal of repetitive regions, to make such sequencing reactions more accurate and efficient.

EXAMPLES

Example 1: Pyrophosphorolysis Dependent Release of the Target Sequence of Interest 1. Bead Preparation 1 ul of beads (ThermoFisher Dynabeads MyOne Streptavidin T1 cat. 65601) per sample were put into a 1.5 mL Eppendorf tube. Up to 100 uL beads can be blocked with 1 mL of blocking solution. The tube was then placed on a magnet followed by removal of the storage buffer. To the tube was then added 1 mL of blocking buffer (1×PBS with 1 ug/mL tRNA) followed by rotation (40 rpm) at room temperature (RT) for 30 minutes.

2. Oligonucleotide Annealing

Dilutions of oligonucleotides in 1×AB buffer (Tris HCl pH=7.5 1 mM, NaCl 50 mL, EDTA 0.2 mM) were prepared.
Probe $A_0$ 20 nM
20 nM fully complementary oligonucleotide 20 nM or mismatched oligonucleotide up to 50 uL
The resulting mixtures were then incubated at 95° C. for 5 minutes and then allowed to slowly cool to room temperature.
After oligonucleotide mixtures were cooldown, the mix was diluted by 1000-fold.

Probe $A_0$ (SEQ ID NO 1):
5'-/5Biosg/TTTTTTTTTTTTTTTTTACCTTATACACCGTGCCGA

ACGCACCGGAGCCCAGCAC-3'
where /5Biosg/ represents a biotin on 5' end

Fully complementary oligonucleoticle (SEQ ID NO 2):
5'-CCCAACCAAGCTCTCTTGAGGATCTTGAAGGAAACTGAATTCAAAAA

GATCAAAGTGCTGGGCTCCGGTGCGTTCGGCACGGTGTATAAGGTAAGGT

CCC-3'

Mismatched oligonucleotide (SEQ ID NO 3):
5'-CCCAACCAAGCTCTCTTGAGGATCTTGAAGGAAACTGAATTCAAAAA

GATCAAAGTGCTGGCCTCCGGTGCGTTCGGCACGGTGTATAAGGTAAGGT

CCC-3'

3. Attachment of Oligonucleotides to Beads

The blocked beads were spun down for 5 seconds in mini-centrifuge at 2000×g and placed on top of a magnet followed by removal of the blocking solution by aspiration. To the tube was then added 10 uL of 2×Binding buffer (TrisHCl pH=7.5 40 mM, NaCl 1 M, EDTA 2 mM, TWEEN20 0.02%) per every 1 uL of beads.

The ratio of beads/oligos and buffer was as follows:
40 uL of 2×Binding buffer
10 uL of beads
50 uL of annealed oligonucleotides diluted 1000 fold.
The tube was then rotated (40 rpm) for 30 minutes at room temperature.

4. Wash Step

The beads were then washed with a 100 uL 1×Washing buffer (TrisHCl pH=7.5 20 mM, NaCl 0.5 M, EDTA 1 mM, TWEEN20 0.1%) one time.

5. Exchange Beads Wash Buffer to 100 uL 1×BFF6 Buffer with 0.01% Triton-X
1×BFF6 with 0.01% Triton-X composition
Tris Acetate pH=7.0 10 mM
Potassium Acetate 30 mM
Magnesium Acetate 17.125 mM
TWEEN20 0.01%

6. Pyrophosphorolysis

The 1×BFF6 0.01% Triton-X buffer was then removed and a PPL mixture (stored at 4° C.) was added to the beads.
The PPL mixture consisted of:
1×BFF6 with 0.1% TWEEN20
10 U/mL Klenow (exo-)
2 U/mL Apyrase
0.5 mM PPi
Total volume 10 uL
The resulting mixture was incubated at 45° C. for 30 minutes.

7. Inactivation of PPi 2.5 uL of TIPP mixture was added to inactivated PPi.
The TIPP mixture consisted of:
1×BFF6 with 0.1% TWEEN20
16 U/mL of TIPP
10 uL of mix from point 6.
Total volume 12.5 uL
The resulting mixture was incubated at 37° C. for 5 minutes.

8. Release of Target of Interest and Detection

The mixture from point 7 was heated up to 60° C. for 5 min. Tubes with the mixture were transferred to the magnetic rack placed at a hot plate set up at 60° C. in order to separate magnetic beads from supernatant.

2 uL of clear supernatant was added to the detection mix consisting of:
1×QSU buffer
0.4 mM dNTPs
0.2 uM Primer mix
20 U/mL Q5U DNA polymerase
10 U/mL UDG
1× SybrGreenl
Total volume: 12.5 uL
Q5 Buffer
The Q5 buffer composition is not publicly available.

```
Primer mix:
Fwd (SEQ ID NO 4):
5'-C*C*C*AACCAAGCTCTCTTGAGGATCTTG-3'

Rev (SEQ ID NO 5):
5'-/5Phos/GGGACCTTACCTTATACACCGTGCCG-3'
where * represents a phosphorothioate bond,
/5Phos/ represent 5' end phosphate
```

Figure 4:
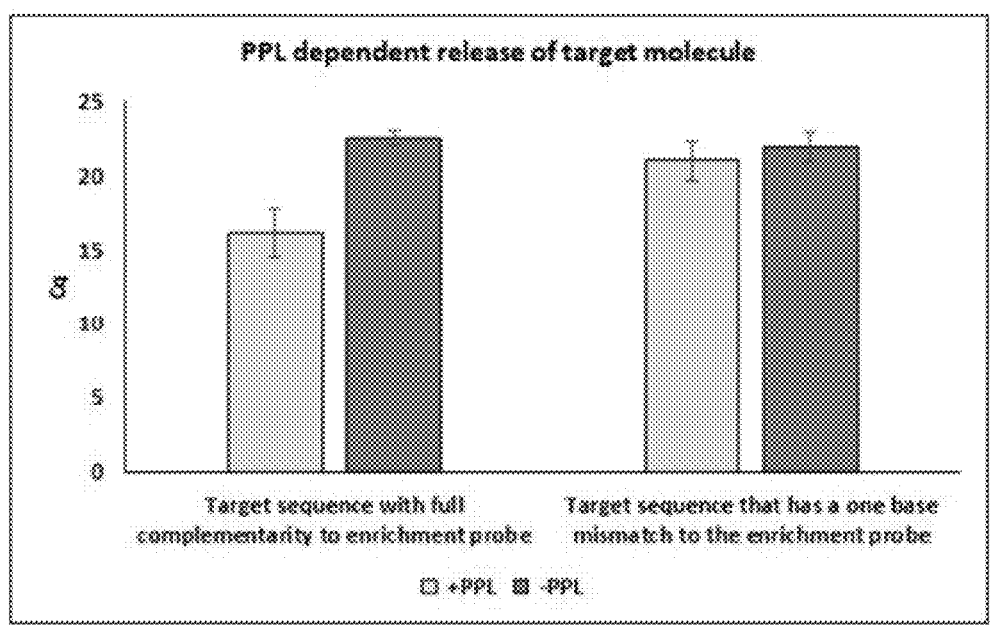
FIG. 4: Pyrophosphorolysis dependent release of target molecule. The lower the Cq value, the more target sequence that has been released into the supernatant from beads. The Cq value is lower for a target sequence that is fully complementary to the enrichment probe when the pyrophosphorolysis reaction is performed. This indicates that the target of interest was released from beads. There was no difference in the Cq values for the mismatched target sequence, regardless of whether the pyrophosphorolysis reaction is performed. This indicates that the mismatched target stayed on beads and wasn't released to supernatant.

The resulting mixture was then incubated as indicated below:
37° C. 1 min
55° C. 10 min
98° C. 1 min
(98° C. 10 sec
63° C. 15 sec
72° C. 15 sec)×50
72° C. 5 min
4° C. pause Fluorescent readings were taken after every cycle in the fam channel. The results can be seen in FIG. 4.

Example 2: Pyrophosphorolysis Dependent Enrichment of the Target Sequence of Interest 1. Bead Preparation 1 ul of beads (ThermoFisher Dynabeads MyOne Streptavidin T1 cat. 65601) per sample was put into a 1.5 mL Eppendorf tube. Up to 100 uL beads can be blocked with 1 mL of blocking buffer. The tube was placed on a magnet followed by removal of the storage buffer. 1 mL of blocking buffer (1×PBS with 1 ug/mL tRNA, Triton-X 0.1%) was added to the tube, followed by rotation (40 rpm) at room temperature (RT) for 30 minutes.

2. 1% MAF and 10% MAF Sample Preparation

1% MAF: 100 nM of Wild-Type oligonucleotide was mixed with 1 nM of Mutant oligonucleotide in the final volume of 100 µL.

10% MAF: 100 nM of Wild-Type oligonucleotide was mixed with 10 nM of Mutant oligonucleotide in the final volume of 100 µL.

```
Wild-Type oligonucleotide (SEQ ID NO 6):
5'-CATCTGCCTCACCTCCACCGTGCAGCTCATCACGCAGCTCATGCCCT

TCGGCTGCCTCCTGGACTATGTCCGGGAACACAAAGACAATAT-3'

Mutant oligonucleotide (SEQ ID NO 7):
5'-C*G*T*ACTGGTGAAAACACCGCAGGCTCATCATGCAGCTCATGCCC TTCGGCTGCCTCCTGGACTGGAAGAGAAAGAATACCATGCAGAAGG-3'
where * represents a phosohorothioate bond
```

3. Oligonucleotide Annealing

Dilutions of oligonucleotides in 1×AB buffer (Tris HCl pH=7.5 1 mM, NaCl 50 mM, EDTA 0.2 mM) were prepared.
Probe $A_0$ 20 nM
10 uL of 1% MAF or 10% MAF sample
made up to 50 uL with nuclease free water.

The resulting mixtures were then incubated at 95° C. for 5 minutes and then allowed to slowly cool to room temperature.

After oligonucleotide mixtures were cooled down, the mix was diluted by 1000-fold.

```
Probe A₀ (SEQ ID NO 8):
5'-/5Biosg/TTTTTTTTTTTTTTTTTTTTCCAGGAGGCAGCCGAAGG

GCATGAGCTGCATGATG-3'
where /5Biosg/ represents a biotin on 5' end
```

4. dPCR Quantification of Targets Pre-Bead Prep

Concentrations of the Wild-Type and Mutant oligonucleotides in the annealed and diluted mixtures were quantified using dPCR. 1000-fold dilution of 1% MAF and 10% MAF samples (taken from point 3) were further diluted 20-fold, followed by a serial dilution of 1:1, 6 times to create reference curve.

The dPCR mixture consisted of:
1×Q5U buffer
0.4 mM dNTPs
0.2 µM Primer mix
20 U/mL Q5U polymerase
10 U/mL UDG
2× EvaGreen
0.0003 µg/mL Alexa 700
0.2% TWEEN20
4 µL DNA template
Total volume: 12 µL
Q5 Buffer
The Q5 buffer composition is not publicly available.

```
Primer mix:
FWD (SEQ ID NO 9):
5'-G*C*C*TCCCTCGCGCCATCAGCATCTGCCTCACCTCCACCG-3'

REV (SEQ ID NO 10):
5'-/5Phos/GCCTTGCCAGCCCGCTCAGATATTGTCTTTGTGTTCCCGG

A-3'
Or

FWD (SEQ ID NO 11):
5'-A*C*G*TACTGGTGAAAACACCGCAG-3'

REV (SEQ ID NO 12):
5'-/5Phos/GCCTCCTTCTGCATGGTATTCTTT-3'
where * represents a phosphorothioate bond,
/5Phos/ represent 5' end phosphate, and a
different primer mix was used for quantification
of the Wild-Type and Mutant oligonucleotides.
```

The resulting mixture was then incubated as indicated below:
37° C. 1 min
55° C. 10 min
98° C. 1 min
(98° C. 10 sec
63° C. 15 sec
72° C. 15 sec)×30
72° C. 5 min
35° C. pause Fluorescent readings were taken after incubation, and the dPCR manufacturer software used for quantification of the different oligos.

5. Attachment of Oligonucleotides to Beads

The blocked beads were spun down for 5 seconds in mini-centrifuge at 2000×g and placed on top of a magnet followed by removal of the blocking solution by aspiration. 10 uL of 2× Binding buffer (TrisHCl pH=7.5 40 mM, NaCl 1 M, EDTA 2 mM, TWEEN20 0.02%) was added to the tube per every 1 μL of beads.

The ratio of beads/oligos and buffer was as follows:
40 μl of 2× Binding buffer
104 of beads
50 μL of annealed oligonucleotides diluted 1000 fold (from point 3).

The tube was then rotated (40 rpm) for 30 minutes at room temperature.

6. Wash Step

The beads were then washed with a 100 μL 1×Washing buffer (TrisHCl pH=7.5 20 mM, NaCl 0.5 M, EDTA 1 mM, TWEEN20 0.1%) one time.

7. Exchange Beads Wash Buffer to 100 μl 1×BFF6 Buffer with 0.01% TWEEN20

1×BFF6 with 0.01% TWEEN20 composition
Tris Acetate pH=7.0 10 mM
Potassium Acetate 30 mM
Magnesium Acetate 17.125 mM
TWEEN20 0.01%

8. Pyrophosphorolysis

The 1×BFF6 0.01% TWEEN20 buffer was then removed and a PPL mixture (stored at 4° C.) was added to the beads.
The PPL mixture consisted of:
1×BFF6 with 0.1% TWEEN20
20 U/mL Klenow (exo-)
2 U/mL Apyrase
0.5 mM PPi
Total volume 20 μL The resulting mixture was incubated at 40° C. for 1 minute.

1×BFF6 with 0.1% TWEEN20 composition
Tris Acetate pH=7.0 10 mM
Potassium Acetate 30 mM
Magnesium Acetate 17.125 mM
TWEEN20 0.1%

9. Inactivation of PPi

5 μL of TIPP mixture was added to inactivate PPi.
The TIPP mixture consisted of:
1×BFF6 with 0.1% TWEEN20
16 U/mL of TIPP
20 μl of mix from point 8.
Total volume 25 μL The resulting mixture was incubated at 37° C. for 5 minutes.

10. Release of Target of Interest and Detection

The mixture from point 9 was heated up to 60° C. for 10 min. Tubes with the mixture were transferred to the magnetic rack placed on a hot plate set up at 60° C. to separate magnetic beads from supernatant.

11. dPCR Quantification of Targets Released from Beads

Concentrations of the Wild-Type and Mutant oligonucleotides in the supernatant were then quantified using dPCR.

4 μL of clear supernatant was added to the detection mix consisting of:
1×Q5U buffer
0.4 mM dNTPs
0.2 μM Primer mix
20 U/mL Q5U DNA polymerase
10 U/mL UDG
2× EvaGreen
0.0003 μg/mL Alexa 700 0.0003 μg/mL
0.2% TWEEN20
Total volume: 12 μL Q5 Buffer The Q5 buffer composition is not publicly available.

```
Primer mix:
FWD (SEQ ID NO 9):
5'-G*C*C*TCCCTCGCGCCATCAGCATCTGCCTCACCTCCACCG-3'

REV (SEQ ID NO 10):
5'-/5Phos/GCCTTGCCAGCCCGCTCAGATATTGTCTTTTGTGTTCCCG
GA-3'
Or

FWD (SEQ ID NO 11):
5'-A*C*G*TACTGGTGAAAACACCGCAG-3'

REV (SEQ ID NO 12):
5'-/5Phos/GC:CTCCTTCTGCATGGTATTCTTT-3'
where * represents a phosphorothioate bond,
/5Phos/ represent 5' end phosphate, and a
different primer mix was used for quantification
of the Wild-Type and Mutant oligonucleotide.
```

The resulting mixture was then incubated as indicated below:
37° C. 1 min
55° C. 10 min
98° C. 1 min
(98° C. 10 sec
63° C. 15 sec
72° C. 15 sec)×30
72° C. 5 min
35° C. pause Fluorescent readings were taken after incubation, and the dPCR manufacturer software used for quantification of the different oligos.

Results for the quantification of oligonucleotides are shown in the Table below.

| Sample | Concentration (copies/uL) | | | | | |
| --- | --- | --- | --- | --- | --- | --- |
| (nominal | Wild-Type | Mutant | Wild-Type | Mutant | Measured mutant fraction | |
| mutant fraction) | before enrichment | before enrichment | after enrichment | after enrichment | Before enrichment | After Enrichment |
| 1% | 18100 | 97 | 273 | 84 | 0.51% | 23.5% |
| 10% | 22307 | 1225 | 412 | 169 | 5.2% | 29.1% |

Example 3: Analysis of EGFR Exon 20 T790M Variant

1. Beads Preparation a. Bead blocking step

Take 1 μL of beads per sample and put into a 1.5 mL eppendorf tube (ThermoFisher Dynabeads MyOne Streptavidin C1 cat. 65001). Up to 100 μL beads can be blocked with 1 mL of blocking solution.

Place the tube with beads on a magnet and wait until the beads will separate and the solution will be clear.

Remove storage buffer.

Add to the tube with beads a 1 mL blocking buffer (1×PBS, 0.1% Tween-20, 1 μg/mL t-RNA).

Rotate at RT for 30 min at 15 rpm.

b. Buffer exchange

Spin down beads and place them on the magnet. Wait until the beads will separate and the solution will be clear.

Remove blocking solution.

Add 10 μL of the 2× Binding buffer (TrisHCl pH=7.5 40 mM, NaCl 1M, EDTA 2 mM, TWEEN20 0.02%) for every 1 μL of beads.

Mix beads by vortexing for 5 seconds.

2. Oligonucleotide Hybridisation

Prepare dilution of oligonucleotides in 1×SSC buffer (5×SSC, 5×Denhardt's solution, 5 mM EDTA, 0.1% SDS)

Probe oligonucleotide 2 pM

WT or Mutant oligonucleotide 0.2/2 fM

Prepare 50 μL of the oligonucleotide per 1 μL of beads.

Incubate at 95° C. for 5 min and at 50/60° C. for 72 hours.

```
Probe oligonucleotide (SEQ ID NO 13):
5'-/5BiosgTTTTTTTTTTTTTTTTTTTCCAGGAGGCAGCCGAAGG

GCATGAGCTGCATGATG-3'

WT oligonucleotide (SEQ ID NO 14):
5'-CTGGTCCCTCATTGCACTGTACTCCCATCTGCCTCACCTCCACCGT

GCAGCTCATCACGCAGCTCATGCCCTTCGGCTGCCTCCTGGACTATGTC

CGGGAACACAAAGACAATATGTGTCGAGAATATCCAAGAGACAGGTTTC

T-3'

Mutant oligonucleotide (SEQ ID NO 15):
5'-CTGGTCCCTCATTGCACTGTACTCCACGTACTGGTGAAAACACCGC

AGGCTCATCATGCAGCTCATGCCCTTCGGCTGCCTCCTGGACTGGAAGA

GAAAGAATACCATGCAGAAGGAGGCGTGTCGAGAATATCCAAGAGACAG

GTTTCT-3'
```

Where/5Biosg/stands for biotin on the 5' end.

3. Attachment Oligonucleotides to the Beads

Mix beads and oligonucleotides in the following ratio:

40 μL of 2× Binding buffer

10 μL of beads from step 1.

50 μL of oligonucleotides from step 2.

Rotate for 30 min at RT at 15 rpm.

4. Bead Washing

After the attachment step is finished—spin down the samples and place them on the magnet and wait 7 minutes.

Remove 80 μL of 100 μL supernatant and add 100 μL of 1×Wash buffer (TrisHCl pH=7.5 20 mM, NaCl 0.5M, EDTA 1 mM, TWEEN20 0.1%).

Vortex samples for 10 seconds and spin them down.

Place samples on the magnet and wait 2 minutes.

Remove 90 μL of 120 μL supernatant and add 100 μL of 1×Wash buffer.

Mix samples by changing the samples position on the magnet—10 times. Wait 2 min.

Remove the whole supernatant and add 100 μL of 1×Wash buffer.

Mix by changing the sample position on the magnet—10 times. Wait 2 min.

Remove whole supernatant and take the samples out of the magnet and add 100 μL 1×BFF6 buffer (Tris Acetate pH=7.0 10 mM, Potassium Acetate 30 mM, Magnesium Acetate 17.125 mM, TWEEN20 0.01%).

Spin the samples down and place the samples on the magnet and wait 2 min.

Remove 1×BFF6 buffer.

5. PPL Reaction

Add PPL mix to the beads kept at 4° C. PPL has the following composition:

1×BFF6-0.1% Tween-20

20 U/mL Klenow (exo-)

2 U/mL Apyrase

+/−0.05 mM PPi

Total volume: 20 μL

Incubate at 40° C. for 10 min, 4° C. pause

6. TIPP Reaction

When the PPL reaction reaches 4° C., add 5 μL of TIPP mixture having:

1×BFF6-0.1% Tween-20

16 U/mL TIPP

20 μL of mixture from step 5.

Total volume: 25 μL

Incubate at 37° C. for 5 min, 60° C. 10 min, 60° C. pause

7. Preamplification

Place the samples from step 6 on the magnet kept on the hot plate and heat up to 60° C.

After the beads are separated take 2 μL of supernatant and add to the following mixture:

1×Q5U buffer dNTPs 0.4 mM

Primer mix 1 0.1 μM

Q5U polymerase 20 U/mL

UDG 10 U/mL

Total volume: 12.5 μL

Q5U buffer:

Primer mix 1 has:

```
Forward primer (SEQ ID NO 16):
5'-AGAAACCTGTCTCTTGGATATTCTCGACAC-3'

Reverse primer (SEQ ID NO 17):
5'-CTGGTCCCTCATTGCACTGTACTCC-3'
```

Place sample in the thermocycler and incubate with lid on 105° C.

1. UDG 37° C. 1 min
2. Int.denaturation 98° C. 1 min
3. Denaturation 98° C. 10 sec
4. Annealing 63° C. 15 sec
5. Elongation 72° C. 15 sec
6. Final elongation 72° C. 5 min
7. Cool down 4° C. hold Step 3-5 repeated 12×

8. dPCR Quantification

After preamplification from step 7 is finished. Add 2 μL of mixture from step 7 to the reaction containing the following:

1×Q5U buffer dNTPs 0.4 mM

Primer mix 2 or 3 0.2 μM

Q5U polymerase 20 U/mL

EvaGreen dye 2×

Alexa Fluor 700 dye 0.0003 μg/μL

TWEEN20 0.2%

Total volume: 12 µL
Primer mix 2 has:

```
Forward primer (SEQ ID NO 18):
5'-GCCTTGCCAGCCCGCTCAGATATTGTCTTTGTGTTCCCGGAC-3'

Reverse prrner (SEQ ID NO 19):
5'-GCCTCCCTCGCGCCATCAGCATCTGCCTCACCTCCACCG-3'
```

Primer mix 3 has:

```
Forward primer (SEQ ID NO 20):
5'-ACGTACTGGTAAAACACCGCAG-3'

Reverse primer (SEQ ID NO 21):
5'-GCCTCCTTCTGCATGGTATTCTTT-3'
```

Figure 5:
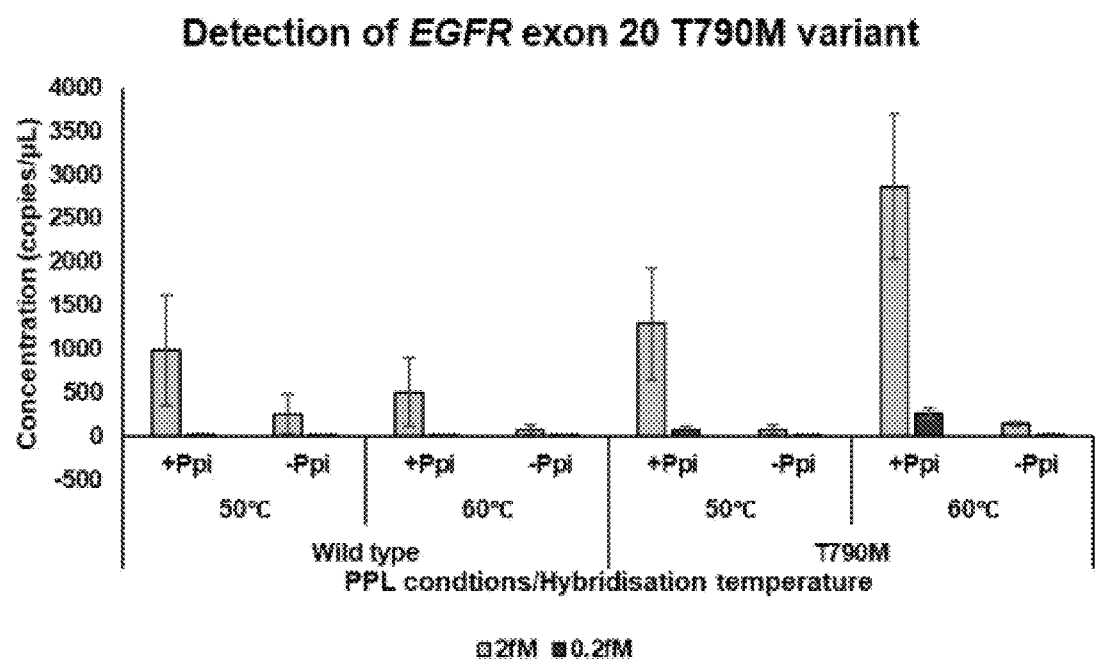
FIG. 5: Detection of EGFR exon 20 T790M variant. The graph shows PPi dependent detection of T790M. By increasing the temperature of the hybridisation step to 60° C., more T790M variant molecules are recovered. Increasing the temperature of the hybridisation step to 60° C. reduces recovery of the WT (Wild type) molecules. In the given conditions 0.2 fM of the T790M variant molecules can be detected.

Place sample in the QIAcuity Digital PCR System with lid on 105° C.
1. Int.denaturation 98° C. 1 min
2. Denaturation 98° C. 10 sec
3. Annealing 63° C. 15 sec
4. Elongation 72° C. 15 sec
5. Final elongation 72° C. 5 min
6. Cool down 35° C. 1 min
Step 2-4 repeated 30×
Take a picture of the partitions in green and yellow channels with exposure duration 600 and 700 ms respectively and gain 6 and 8 respectively. Data obtained from such an experiment is shown in FIG. 5.

Example 4: Detection of the EGFR Exon 20 T790M Variant at a Different Variant Allele Fraction (VAF)

1. Beads Preparation
Bead Blocking Step
  Take 1 µL of beads per sample and put into a 1.5 mL eppendorf tube (ThermoFisher Dynabeads MyOne Streptavidin C1 cat. 65001). Up to 100 µL beads can be blocked with 1 mL of blocking solution.
  Place the tube with beads on a magnet and wait until the beads will separate and the solution will be clear.
  Remove storage buffer.
  Add to the tube with beads a 1 mL blocking buffer (1×PBS, 0.1% Tween-20, 1 µg/mL t-RNA).
  Rotate at RT for 30 min at 15 rpm.
Buffer Exchange
  Spin down beads and place them on the magnet. Wait until the beads will separate and the solution will be clear.
  Remove blocking solution.
  Add 10 µL of the 2× Binding buffer (TrisHCl pH=7.5 40 mM, NaCl 1M, EDTA 2 mM, TWEEN20 0.02%) for every 1 µL of beads.
  Mix beads by vortexing for 5 seconds.
2. Oligonucleotide Hybridisation
  Prepare dilution of oligonucleotides in 1×SSC buffer (5×SSC, 5×Denhardt's solution, 5 mM EDTA, 0.1% SDS)
  Probe oligonucleotide 2 pM
  WT 0-200 fM
  Mutant oligonucleotide 0.2-100 fM
  Prepare 50 µL of the oligonucleotide per 1 µL of beads.
  Incubate at 95° C. for 5 min and at 60° C. for 72 hours.

```
Probe oligonucleotide (SEQ ID 13):
5'-/5Biosg/TTTTTTTTTTTTTTTTTTTTCCAGGAGGCAGCCGAAG
GGCATGAGCTGCATGATG-3'

WT oligonucleotide (SEQ ID 14):
5'-CTGGTCCCTCATTGCACTGTACTCCCATCTGCCTCACCTCCACCGT
GCAGCTCATCACGCAGCTCATGCCCTTCGGCTGCCTCCTGGACTATGTC
CGGGAACACAAAGACAATATGTGTCGAGAATATCCAAGAGACAGGTTTC
T-3'

Mutant oligonucleotide (SEQ ID 15):
5'-CTGGTCCCTCATTGCACTGTACTCCACGTACTGGTGAAAACACCGC
AGGCTCATCATGCAGCTCATGCCCTTCGGCTGCCTCCTGGACTGGAAGA
GAAAGAATACCATGCAGAAGGAGGCGTGTCGAGAATATCCAAGAGACAG
GTTTCT-3'
```

Where/5Biosg/stands for biotin on the 5' end.
3. Attachment Oligonucleotides to the Beads
  Mix beads and oligonucleotides in the following ratio:
  40 µl of 2× Binding buffer
  10 µL of beads from step 1.
  50 µL of oligonucleotides from step 2.
  Rotate for 30 min at RT at 15 rpm.
4. Bead Washing
  After the attachment step is finished—spin down the samples and place them on the magnet and wait 7 minutes.
  Remove 80 µL of 100 µL supernatant and add 100 µL of 1×Wash buffer (TrisHCl pH=7.5 20 mM, NaCl 0.5M, EDTA 1 mM, TWEEN20 0.1%).
  Vortex samples for 10 seconds and spin them down.
  Place samples on the magnet and wait 2 minutes.
  Remove 90 µL of 120 µL supernatant and add 100 µl of 1×Wash buffer.
  Mix samples by changing the samples position on the magnet—10 times. Wait 2 min.
  Remove the whole supernatant and add 100 µL of 1×Wash buffer.
  Mix by changing the sample position on the magnet—10 times. Wait 2 min.
  Remove whole supernatant and take the samples out of the magnet and add 100 µL 1×BFF6 buffer (Tris Acetate pH=7.0 10 mM, Potassium Acetate 30 mM, Magnesium Acetate 17.125 mM, TWEEN20 0.01%).
  Spin the samples down and place the samples on the magnet and wait 2 min.
  Remove 1×BFF6 buffer.
5. PPL Reaction
  Add PPL mix to the beads kept at 4° C. PPL has the following composition:
  1×BFF6-0.1% Tween-20
  20 U/mL Klenow (exo-)
  2 U/mL Apyrase
  +/−0.05 mM PPi
  Total volume: 20 µL
  Incubate at 40° C. for 10 min, 4° C. pause
6. TIPP Reaction
  When the PPL reaction reaches 4° C., add 5 µL of TIPP mixture having:
  1×BFF6-0.1% Tween-20
  16 U/mL TIPP
  20 µL of mixture from step 5.
  Total volume: 25 µL Incubate at 37° C. for 5 min, 60° C. 10 min, 60° C. pause 7. Preamplification Place the samples from step 6 on the magnet kept on the hot plate and heat up to 60° C.

After the beads are separated take 24 of supernatant and add to the following mixture:

1×Q5U buffer
dNTPs 0.4 mM
Primer mix 1 0.1 μM
Q5U polymerase 20 U/mL
UDG 10 U/mL
Total volume: 12.5 μL
Q5U buffer:
Primer mix 1 has:

```
Forward primer (SEQ ID 16):
5'-AGAAACCTGTCTCTTGGATATTCTCGACAC-3'

Reverse primer (SEQ ID 17):
5'-CTGGTCCCTCATTGCACTGTACTCC-3'
```

Place sample in the thermocycler and incubate with lid on 105° C.

1. UDG 37° C. 1 min
2. Int.denaturation 98° C. 1 min
3. Denaturation 98° C. 10 sec
4. Annealing 63° C. 15 sec
5. Elongation 72° C. 15 sec
6. Final elongation 72° C. 5 min
7. Cool down 4° C. hold Step 3-5 repeated 12×

8. dPCR Quantification

After preamplification from step 7 is finished. Add 2 μL. of mixture from step 7 to the reaction containing the following:

1×Q5U buffer
dNTPs 0.4 mM
Primer mix 2 or 3 0.2 μM
Q5U polymerase 20 U/mL
EvaGreen dye 2×
Alexa Fluor 700 dye 0.0003 μg/μL
TWEEN20 0.2%
Total volume: 12 μL
Primer mix 2 has:

```
Forward primer (SEQ ID 18):
5'-GCCTTGCCAGCCCGCTCAGATATTGTCTTTGTGTTCCCGGAC-3'

Reverse prrner (SEQ ID 19):
5'-GCCTCCCTCGCGCCATCAGCATCTGCCTCACCTCCACCG-3'
```

Primer mix 3 has:

```
Forward primer (SEQ ID 20):
5'-ACGTACTGGTAAAACACCGCAG-3'

Reverse primer (SEQ ID 21):
5'-GCCTCCTTCTGCATGGTATTCTTT-3'
```

Place sample in the QIAcuity Digital PCR System with lid on 105° C.

1. Int.denaturation 98° C. 1 min
2. Denaturation 98° C. 10 sec
3. Annealing 63° C. 15 sec
4. Elongation 72° C. 15 sec
5. Final elongation 72° C. 5 min
6. Cool down 35° C. 1 min Step 2-4 repeated 30×

Figure 6:
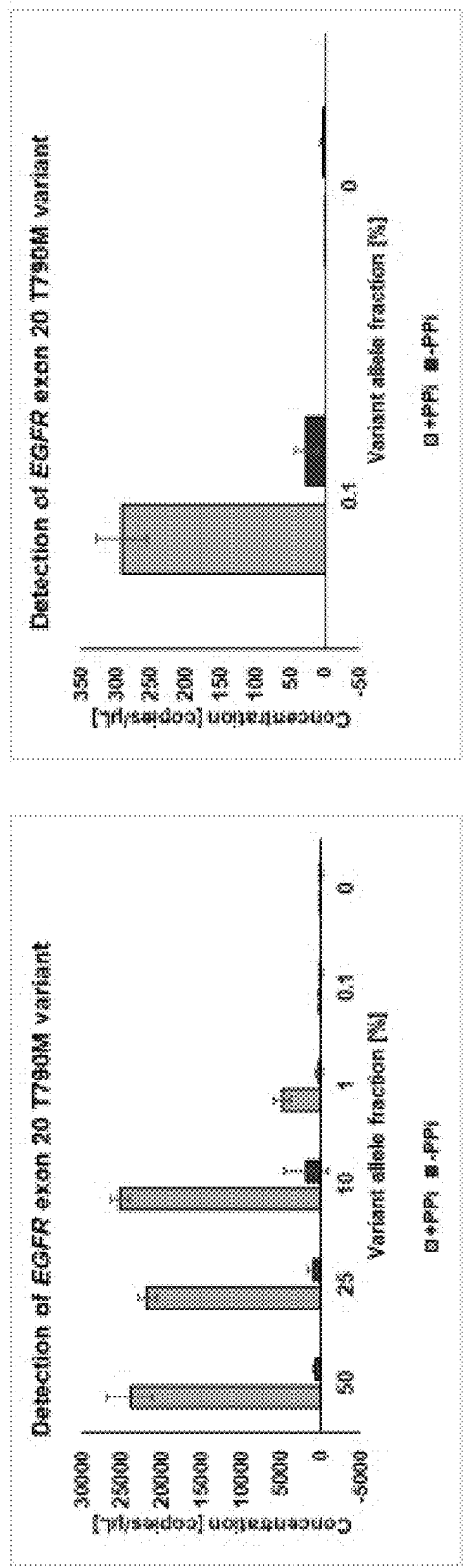
FIG. 6: Detection of the EGFR exon 20 T790M variant at a different variant allele fraction (VAF). Showing PPi-dependent detection as low as 0.1% VAF.

Take a picture of the partitions in green and yellow channels with exposure duration 600 and 700 ms respectively and gain 6 and 8 respectively. Data obtained from such an experiment is shown in FIG. 6.

Example 5: Effect of Hybridisation Buffer and Time of Hybridization on Detection of EGFR Exon 20 T790M Variant at 0.1% VAF 1. Beads Preparation a. Bead blocking step Take 1 μL of beads per sample and put into a 1.5 mL eppendorf tube (ThermoFisher Dynabeads MyOne Streptavidin C1 cat. 65001). Up to 1004 beads can be blocked with 1 mL of blocking solution.

Place the tube with beads on a magnet and wait until the beads will separate and the solution will be clear.

Remove storage buffer.

Add to the tube with beads a 1 mL blocking buffer (1×PBS, 0.1% Tween-20, 1 μg/mL t-RNA).

Rotate at RT for 30 min at 15 rpm.

b. Buffer exchange

Spin down beads and place them on the magnet. Wait until the beads will separate and the solution will be clear.

Remove blocking solution.

Add 10 μl of the 2× Binding buffer (TrisHCl pH=7.5 40 mM, NaCl 1M, EDTA 2 mM, TWEEN20 0.02%) for every 1 μL of beads.

Mix beads by vortexing for 5 seconds.

2. Oligonucleotide Hybridisation

Prepare dilution of oligonucleotides in:

Buffer 1: 1×SSC buffer (5×SSC, 5×Denhardt's solution, 5 mM EDTA, 0.1% SDS) or

Buffer 2: ULTRAhyb™ Ultrasensitive Hybridization Buffer (cat no. AM8670) or

Buffer 3: 1×SSC+DS buffer (5×SSC, 5×Denhardt's solution, 5 mM EDTA, 0.1% SDS, 5% dextran sulphate)

Probe oligonucleotide 2 pM
   WT oligonucleotides mix 198 fM
   Mutant oligonucleotides mix 2 fM
   Genomic DNA 380 ng Prepare 50 μL of the oligonucleotide per 1 μL of beads Incubate at 95° C. for 5 min and at 60° C. for ⅓ hours.

Probe oligonucleotide (SEQ ID 12):

```
5'-/5Biosg/TTTTTTTTTTTTTTTTTTTTCCAGGAGGCAGCCGAAG
GGCATGAGCTGCATGATG-3'
```

Where/5Biosg/stands for biotin on the 5' end.

WT oligonucleotides mix has:

```
Forward strand 1 (SEQ ID NO 22):
5'-AATGATACGGCGACCACCGAGATCTACACTGGTAATTACCGACGAA

AACGGCCCGTGCAGCTCATCACGCAGCTCATGCCCTTCGGCTGCCTCCT

GGACTATGTCCGGGAACCGCAAGACTGTAACCACGCGTATCTCGTATGC

CGTCTTCTGCTTG-3'

Reverse strand 2 (SEQ ID NO 23):
5'-CAAGCAGAAGACGGCATACGAGATACGCGTGGTTACAGTCTTGCGG

TTCCCGGACATAGTCCAGGAGGCAGCCGAAGGGCATGAGCTGCGTGATG

AGCTGCACGGGCCGTTTTCGTCGGTAATTACCAGTGTAGATCTCGGTGG

TCGCCGTATCATT-3'
```

Forward strand 2 (SEQ ID NO 24):
5'-AATGATACGGCGACCACCGAGATCTACACATGAAAGCTGGCTACAG
GAAGGCTCAAAAAGATCAAAGTGCTGGGCTCCGGTGCGTTCGGCACGGT
GTATAAGGTAAGGTCCCAATATTGAAACCCACGGCATGGTGATCTCGTA
TGCCGTCTTCTGCTTG-3'

Reverse strand 2 (SEQ ID NO 25):
5'-CAAGCAGAAGACGGCATACGAGATCACCATGCCGTGGGTTTCAATA
TTGGGACCTTACCTTATACACCGTGCCGAACGCACCGGAGCCCAGCACT
TTGATCTTTTTGAGCCTTCCTGTAGCCAGCTTTCATGTGTAGATCTCGG
TGGTCGCCGTATCATT-3'

Forward strand 3 (SEQ ID NO 26):
5'-AATGATACGGCGACCACCGAGATCTACACCAGCCGCCGCGGTAAGA
TCACAGATTTTGGGCTGGCCAAACTGCTGGGTGCGGAAGAGAAAGAATA
CCATGCAGAGAATTGGCGGGGAGCACATCTCGTATGCCGTCTTCTGCT
TG-3'

Reverse strand 3 (SEQ ID NO 27):
5'-CAAGCAGAAGACGGCATACGAGATGTGCTCCCCCGCCAATTCTCTG
CATGGTATTCTTTCTCTTCCGCACCCAGCAGTTTGGCCAGCCCAAAATC
TGTGATCTTACCGCGGCGGCTGGTGTAGATCTCGGTGGTCGCCGTATCA
TT-3'

Forward strand 4 (SEQ ID NO 28):
5'-AATGATACGGCGACCACCGAGATCTACACGGAAGTGAAAAGTCGTA
ACAAGGCATGATTTTGGTCTAGCTACAGTGAAATCTCGATGGAGTGGGT
CCCATCAGTTTGAACAGTTCTGCATCGATGAAGAACGCAGCATCTCGTA
TGCCGTCTTCTGCTTG-3'

Reverse strand 4 (SEQ ID NO 29):
5'-CAAGCAGAAGACGGCATACGAGATGCTGCGTTCTTCATCGATGCAG
AACTGTTCAAACTGATGGGACCCACTCCATCGAGATTTCACTGTAGCTA
GACCAAAATCATGCCTTGTTACGACTTTTCACTTCCGTGTAGATCTCGG
TGGTCGCCGTATCATT-3'

Forward strand 5 (SEQ ID NO 30):
5'-AATGATACGGCGACCACCGAGATCTACACAGGCGCTGTTTGGTCTC
TTAGCCAGGAAGCATACGTGATGGCTGGTGTGGGCTCCCCATATGTCTC
CCGCCTTCTGGGCATCAGGAATCATTAGCGGTAGCGAATCTCGTATGCC
GTCTTCTGCTTG-3'

Reverse strand 5 (SEQ ID NO 31):
5'-CAAGCAGAAGACGGCATACGAGATTCGCTACCGCTAATGATTCCTG
ATGCCCAGAAGGCGGGAGACATATGGGGAGCCCACACCAGCCATCACGT
ATGCTTCCTGGCTAAGAGACCAAACAGCGCCTGTGTAGATCTCGGTGGT
CGCCGTATCATT-3'

Forward strand 6 (SEQ ID NO 32):
5'-AATGATACGGCGACCACCGAGATCTACACGAGCCGGTAGTGTTGAA
AGGAGGTCCATCATCTCTGCGGTGGTTGGCATTCTGCTGGTCGTGGTCT

TGGGGGTGGTCTTTGGCTTTGCCTGCACTCATTGAAGGATCTCGTATGC
CGTCTTCTGCTTG-3'

Reverse strand 6 (SEQ ID NO 33):
5'-CAAGCAGAAGACGGCATACGAGATCCTTCAATGAGTGCAGGCAAAG
CCAAAGACCACCCCAAGACCACGACCAGCAGAATGCCAACCACCGCAG
AGATGATGGACCTCCTTTCAACACTACCGGCTCGTGTAGATCTCGGTGG
TCGCCGTATCATT-3'

Forward strand 7 (SEQ ID NO 34):
5'-AATGATACGGCGACCACCGAGATCTACACTGGCTCAGGAAGAACGC
AGTTGTGGTAGTTGGAGCTGGTGGCGTAGGCAAGAGTGCCTTGACGATA
CAGCTAATTCAGATGGAGCATGTGGTTTAATTGCGAATCTCGTATGCCG
TCTTCTGCTTG-3'

Reverse strand 7 (SEQ ID NO 35):
5'-CAAGCAGAAGACGGCATACGAGATTCGCAATTAAACCACATGCTCC
ATCTGAATTAGCTGTATCGTCAAGGCACTCTTGCCTACGCCACCAGCTC
CAACTACCACAACTGCGTTCTTCCTGAGCCAGTGTAGATCTCGGTGGTC
GCCGTATCATT-3'

Forward strand 8 (SEQ ID NO 36):
5'-AATGATACGGCGACCACCGAGATCTACACCCTTGGTCATTTAGAGG
AAGTGGCTACTGGTCCCTCATTGCACTGTACTCCTCTTGACCTGCTGTG
TCGAGAATATCCAAGAGACAGGTTTCTCCATGCATCGATGAAGAACGCA
GCATCTCGTATGCCGTCTTCTGCTTG-3'

Reverse strand 8 (SEQ ID NO 37):
5'-CAAGCAGAAGACGGCATACGAGATGCTGCGTTCTTCATCGATGCAT
GGAGAAACCTGTCTCTTGGATATTCTCGACACAGCAGGTCAAGAGGAGT
ACAGTGCAATGAGGGACCAGTAGCCACTTCCTCTAAATGACCAAGGGTG
TAGATCTCGGTGGTCGCCGTATCATT-3'

Mutant oligonucleotides mix has:
Forward strand 1 (SEQ ID NO 38):
5'-AATGATACGGCGACCACCGAGATCTACACTGATTTCCGTGCGTCTG
AATGCCCGTGCAGCTCATCATGCAGCTCATGCCCTTCGGCTGCCTCCTG
GACTATGTCCGGGAACCGAAACACGCTACGGCAGCATATCTCGTATGCC
GTCTTCTGCTTG-3'

Reverse strand 1 (SEQ ID NO 39):
5'-CAAGCAGAAGACGGCATACGAGATATGCTGCCGTAGCGTGTTTCGG
TTCCCGGACATAGTCCAGGAGGCAGCCGAAGGGCATGAGCTGCATGATG
AGCTGCACGGGCATTCAGACGCACGGAAATCAGTGTAGATCTCGGTGGT
CGCCGTATCATT-3'

Forward strand 2 (SEQ ID NO 40):
5'-AATGATACGGCGACCACCGAGATCTACACGTTGAAAATGGTCTGCT
GCTGTTCAAAAGATCAAAGTGCTGGCCTCCGGTGCGTTCGGCACGGTG
TATAAGGTAAGGTCCCTCTGTGGTGGATGAAGCCAATAATCTCGTATGC
CGTCTTCTGCTTG-3'

-continued

Reverse strand 2 (SEQ ID NO 41):
5'-CAAGCAGAAGACGGCATACGAGATTATTGGCTTCATCCACCACAGA

GGGACCTTACCTTATACACCGTGCCGAACGCACCGGAGGCCAGCACTTT

GATCTTTTTGAACAGCAGCAGACCATTTTCAACGTGTAGATCTCGGTGG

TCGCCGTATCATT-3'

Forward strand 3 (SEQ ID NO 42):
5'-AATGATACGGCGACCACCGAGATCTACACGCGGTAATTCCAGCTCC

AAGTGATCACAGATTTTGGGCGTGCCAAACTGCTGGGTGCGGAAGAGAA

AGAATACCATGCAGAGAGAGGTGCAAATTCTGGGATCTATCTCGTATGC

CGTCTTCTGCTTG-3'

Reverse strand 3 (SEQ ID NO 43):
5'-CAAGCAGAAGACGGCATACGAGATAGATCCCAGAATTTGCACCTCT

CTCTGCATGGTATTCTTTCTCTTTCCGCACCCAGCAGTTTGGCACGCCC

AAAATCTGTGATCACTTGGAGCTGGAATTACCGCGTGTAGATCTCGGTG

GTCGCCGTATCATT-3'

Forward strand 4 (SEQ ID NO 44):
5'-AATGATACGGCGACCACCGAGATCTACACGCATCGATGAAGAACGC

AGCTGATTTTGGTCTAGCTACAGAGAAATCTCGATGGAGTGGGTCCCAT

CAGTTTGAACAGTTGTCGCATATCAATAAGCGGAGGAATCTCGTATGCC

GTCTTCTGCTTG-3'

Reverse strand 4 (SEQ ID NO 45):
5'-CAAGCAGAAGACGGCATACGAGATTCCTCCGCTTATTGATATGCGA

CAACTGTTCAAACTGATGGGACCCACTCCATCGAGATTTCTCTGTAGCT

AGACCAAAATCAGCTGCGTTCTTCATCGATGCGTGTAGATCTCGGTGGT

CGCCGTATCATT-3'

Forward strand 5 (SEQ ID NO 46):
5'-AATGATACGGCGACCACCGAGATCTACACTGGCTAGTGGCATTCTG

ATGCGGAAGCATACGTGATGGCTGTGTGTGTGGGCTCCCCATATGTCTC

CCGCCTTCTGGGCATGCAAGGGCGGCTAAAGTATCAATCTCGTATGCCG

TCTTCTGCTTG-3'

Reverse strand 5 (SEQ ID NO 47):
5'-CAAGCAGAAGACGGCATACGAGATTGATACTTTAGCCGCCCTTGCA

TGCCCAGAAGGCGGGAGACATATGGGGAGCCCACACACACAGCCATCAC

GTATGCTTCCGCATCAGAATGCCACTAGCCAGTGTAGATCTCGGTGGTC

GCCGTATCATT-3'

Forward strand 6 (SEQ ID NO 48):
5'-AATGATACGGCGACCACCGAGATCTACACTGCAATGAGGACCGGTA

TATCTCTGTCCATCATCTCTGCGGTGGAAGGCATTCTGCTGGTCGTGGT

CTTGGGGGTGGTCTTTGGTGGAATATTAACACGGGCGTGCATCTCGTAT

GCCGTCTTCTGC

Reverse strand 6 (SEQ ID NO 49):
5'-CAAGCAGAAGACGGCATACGAGATGCACGCCCGTGTTAATATTCCA

CCAAAGACCACCCCCAAGACCACGACCAGCAGAATGCCTTCCACCGCAG

AGATGATGGACAGAGATATACCGGTCCTCATTGCAGTGTAGATCTCGGT

GGTCGCCGTATCATT-3'

Forward strand 7 (SEQ ID NO 50):
5'-AATGATACGGCGACCACCGAGATCTACACGAGGACAGGATTAGATA

CCCGGTTGTGGTAGTTGGAGCTTGTGGCGTAGGCAAGAGTGCCTTGACG

ATACAGCTAATTCAGAGGAAGGTGGGGATGACGTATCTCGTATGCCGTC

TTCTGCTTG-3'

Reverse strand 7 (SEQ ID NO 51):
5'-CAAGCAGAAGACGGCATACGAGATACGTCATCCCCACCTTCCTCTG

AATTAGCTGTATCGTCAAGGCACTCTTGCCTACGCCACAAGCTCCAACT

ACCACAACCGGGTATCTAATCCTGTCCTCGTGTAGATCTCGGTGGTCGC

CGTATCATT-3'

Forward strand 8 (SEQ ID NO 52):
5'-AATGATACGGCGACCACCGAGATCTACACGCTCAGGAAGAACGCTG

GTACTGGTCCCTCATTGCACTGTACTCCTCGTGACCTGCTGTGTCGAGA

ATATCCAAGAGACAGGTTTCTCCATCGAAGTACATGTGTAGCGGTGATC

TCGTATGCCGTCTTCTGCTTG-3'

Reverse strand 8 (SEQ ID NO 53):
5'-CAAGCAGAAGACGGCATACGAGATCACCGCTACACATGTACTTCGA

TGGAGAAACCTGTCTCTTGGATATTCTCGACACAGCAGGTCACGAGGAG

TACAGTGCAATGAGGGACCAGTACCAGCGTTCTTCCTGAGCGTGTAGAT

CTCGGTGGTCGCCGTATCATT-3'

3. Attachment Oligonucleotides to the Beads
   Mix beads and oligonucleotides in the following ratio:
   40 µL of 2× Binding buffer
   10 µL of beads from step 1.
   50 µL of oligonucleotides from step 2.
   Rotate for 30 min at RT at 15 rpm.
4. Bead Washing
   After the attachment step is finished—spin down the samples and place them on the magnet and wait 7 minutes.
   Remove 80 µL of 100 µL supernatant and add 100 µL of 1×Wash buffer (TrisHCl pH=7.5 20 mM, NaCl 0.5M, EDTA 1 mM, TWEEN20 0.1%).
   Vortex samples for 10 seconds and spin them down.
   Place samples on the magnet and wait 2 minutes.
   Remove 90 µL of 120 µL supernatant and add 100 µL of 1×Wash buffer.
   Mix samples by changing the samples position on the magnet—10 times. Wait 2 min.
   Remove the whole supernatant and add 100 µL of 1×Wash buffer.
   Mix by changing the sample position on the magnet—10 times. Wait 2 min.
   Remove whole supernatant and take the samples out of the magnet and add 100 µL 1×BFF6 buffer (Tris Acetate pH=7.0 10 mM, Potassium Acetate 30 mM, Magnesium Acetate 17.125 mM, TWEEN20 0.01%).
   Spin the samples down and place the samples on the magnet and wait 2 min.
   Remove 1×BFF6 buffer
5. PPL Reaction
   Add PPL mix to the beads kept at 4° C. PPL consists of the following composition:
   1×BFF6-0.1% Tween-20
   20 U/mL Klenow (exo-)
   2 U/mL Apyrase 0.05 mM PPi
Total volume: 20 µL
Incubate at 40° C. for 10 min, 4° C. pause 6. TIPP Reaction
When the PPL reaction reaches 4° C., add 5 µL of TIPP mixture having:
1×BFF6-0.1% Tween-20
16 U/mL TIPP
20 µL of mixture from step 5.
Total volume: 25 µl
Incubate at 37° C. for 5 min, 60° C. 10 min, 60° C. pause 7. Preamplification
Place the samples from step 6 on the magnet kept on the hot plate and heat up to 60° C.
After the beads are separated take 2 µL of supernatant and add to the following mixture: 1×Q5U buffer
dNTPs 0.4 mM
Primer mix 4 0.1 µM
Q5U polymerase 20 U/mL
UDG 10 U/mL
Total volume: 12.5 µL
Q5U buffer:
Primer mix 4 has:

```
Forward primer (SEQ ID NO 54):
5'-AATGATACGGCGACCACCGAGATCTACAC-3'

Reverse primer (SEQ ID NO 55):
5'-AATGATACGGCGACCACCGAGATCTACAC-3'
```

Place sample in the thermocycler and incubate with lid on 105° C.
1. UDG 37° C. 1 min
2. Int.denaturation 98° C. 1 min
3. Denaturation 98° C. 10 sec
4. Annealing 63° C. 15 sec
5. Elongation 72° C. 15 sec
6. Final elongation 72° C. 5 min
7. Cool down 4° C. hold
Step 3-5 repeated 12×

8. dPCR Quantification
After preamplification from step 7 is finished. Add 2 µL of mixture from step 7 to the reaction containing the following:
1×Q5U buffer
dNTPs 0.4 mM
Primer mix 5 or 6 0.2 µM
Q5U polymerase 20 U/mL
EvaGreen dye 2×
Alexa Fluor 700 dye 0.0003 µg/µL
TWEEN20 0.2%
Total volume: 12 µL
Primer mix 5 has:

```
Forward primer (SEQ ID NO 56):
5'-TGGTAATTACCGACGAAAACGGC-3'

Reverse primer (SEQ ID NO 57):
5'-ACGCGTGGTTACAGTCTTGCG-3'
```

Primer mix 6 has:

```
Forward primer (SEQ ID NO 58):
5'-TGATTTCCGTGCGTCTGAATGC-3'

Reverse primer (SEQ ID NO 59):
5'-ATGCTGCCGTAGCGTGTTTCG-3'
```

Place sample in the QIAcuity Digital PCR System with lid on 105° C.
1. Int.denaturation 98° C. 1 min
2. Denaturation 98° C. 10 sec
3. Annealing 63° C. 15 sec
4. Elongation 72° C. 15 sec
5. Final elongation 72° C. 5 min
6. Cool down 35° C. 1 min
Step 2-4 repeated 30×

Figure 7:
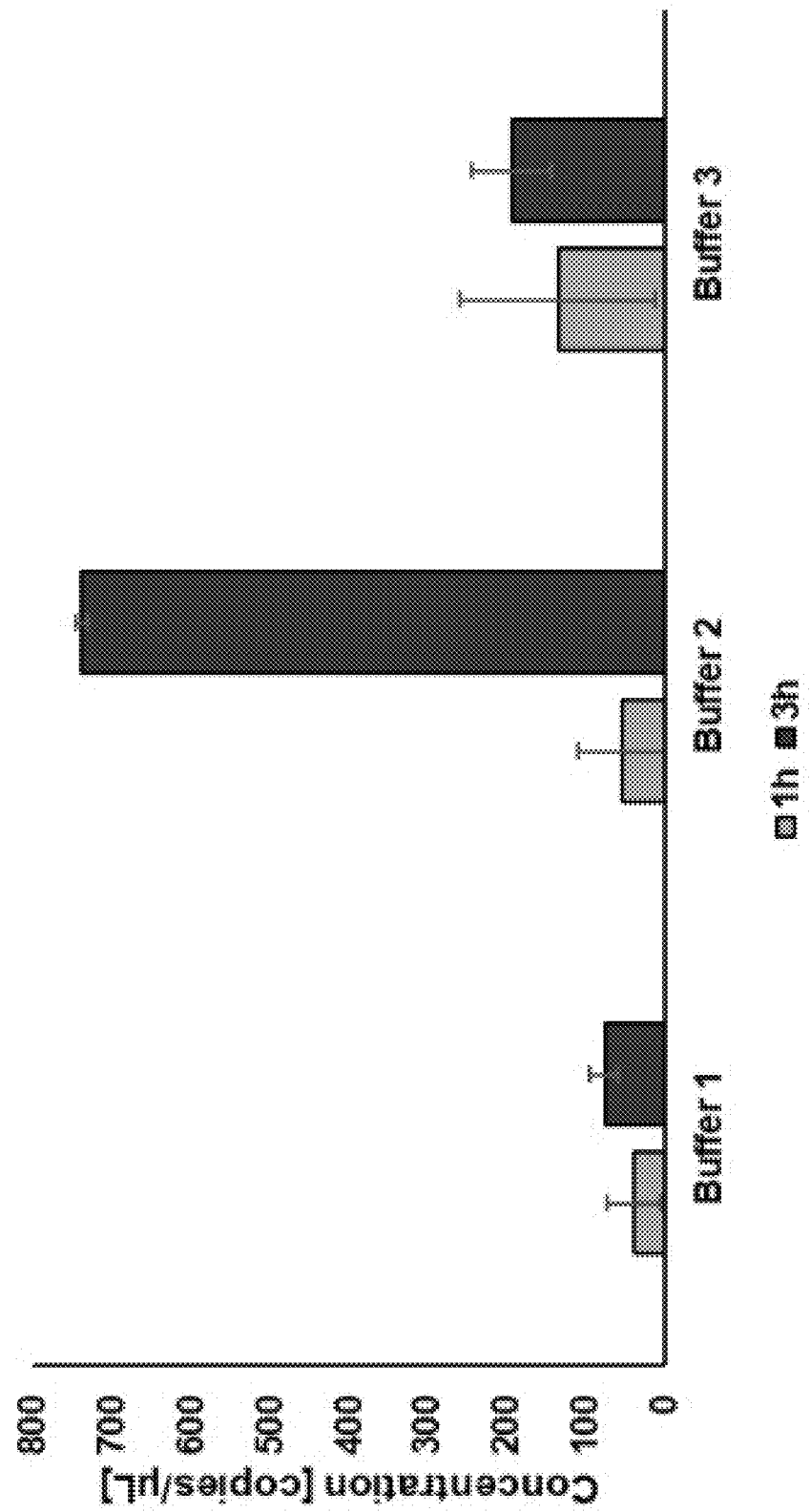
FIG. 7: Effect of hybridisation buffer and time of hybridization on detection of EGFR exon 20 T790M variant at 0.1% VAF. In this particular experiment, one hour of hybridisation is not enough to detect variants of interest. The best performance when using a three hour hybridizations step is achieved with buffer 2 (see Example 3).

Take a picture of the partitions in green and yellow channels with exposure duration 600 and 700 ms respectively and gain 6 and 8 respectively. Data obtained from such an experiment is shown in FIG. 7.

Example 6: Enrichment Factor for the EGFR Exon 20 T790M Variant

1. Beads Preparation
a. Bead Blocking Step
Take 1 µL of beads per sample and put into a 1.5 mL eppendorf tube (ThermoFisher Dynabeads MyOne Streptavidin C1 cat. 65001). Up to 100 µL beads can be blocked with 1 mL of blocking solution.
Place the tube with beads on a magnet and wait until the beads will separate and the solution will be clear.
Remove storage buffer.
Add to the tube with beads a 1 mL blocking buffer (1×PBS, 0.1% Tween-20, 1 µg/mL t-RNA).
Rotate at RT for 30 min at 15 rpm.

b. Buffer Exchange
Spin down beads and place them on the magnet. Wait until the beads will separate and the solution will be clear.
Remove blocking solution.
Add 10 µL of the 2× Binding buffer (TrisHCl pH=7.5 40 mM, NaCl 1M, EDTA 2 mM, TWEEN20 0.02%) for every 1 µL of beads.
Mix beads by vortexing for 5 seconds.

2. Oligonucleotide Hybridisation
Prepare dilution of oligonucleotides in
Buffer 1: 1×SSC buffer (5×SSC, 5×Denhardt's solution, 5 mM EDTA, 0.1% SDS) or
Buffer 2: ULTRAhyb™ Ultrasensitive Hybridization Buffer (Thermo Fisher cat no. AM8670) or
Buffer 3: ULTRAhyb™-Oligo (Thermo Fisher cat no. AM8663) or
Buffer 4: 1×SSC+10% Formide buffer (5×SSC, 5×Denhardt's solution, 5 mM EDTA, 0.1% SDS, 10% Formide) or
Buffer 5: 1×SSC+25% Formide buffer (5×SSC, 5×Denhardt's solution, 5 mM EDTA, 0.1% SDS, 25% Formide) or
Buffer 6: 1×SSC+48% Formide buffer (5×SSC, 5×Denhardt's solution, 5 mM EDTA, 0.1% SDS, 48% Formide)
Probe oligonucleotide 2 pM
WT oligonucleotides mix 198/199.8 fM
Mutant oligonucleotides mix 2/0.2 fM
Genomic DNA 380 ng
Prepare 50 µL of the oligonucleotide per 1 µL of beads
Incubate at 95° C. for 5 min and at 60° C. for ⅓ hours.
WT oligonucleotides mix has SEQ ID NOs 22-37.
Mutant oligonucleotides mix has SEQ ID Nos 38-53.

3. Attachment Oligonucleotides to the Beads
Mix beads and oligonucleotides in the following ratio:
40 µL of 2×Binding buffer
10 µL of beads from step 1.

50 μL of oligonucleotides from step 2.
Rotate for 30 min at RT at 15 rpm.

4. Bead Washing

After the attachment step is finished—spin down the samples and place them on the magnet and wait 7 minutes.

Remove 80 μL of 100 μL supernatant and add 100 μL of 1×Wash buffer (TrisHCl pH=7.5 20 mM, NaCl 0.5M, EDTA 1 mM, TWEEN20 0.1%).

Vortex samples for 10 seconds and spin them down.

Place samples on the magnet and wait 2 minutes.

Remove 90 μL of 120 μL supernatant and add 100 μl of 1×Wash buffer.

Mix samples by changing the samples position on the magnet—10 times. Wait 2 min.

Remove the whole supernatant and add 100 μL of 1×Wash buffer.

Mix by changing the sample position on the magnet—10 times. Wait 2 min.

Remove whole supernatant and take the samples out of the magnet and add 100 μL 1×BFF6 buffer (Tris Acetate pH=7.0 10 mM, Potassium Acetate 30 mM, Magnesium Acetate 17.125 mM, TWEEN20 0.01%).

Spin the samples down and place the samples on the magnet and wait 2 min.

Remove 1×BFF6 buffer.

5. PPL Reaction

Add PPL mix to the beads kept at 4° C. PPL consists of the following composition:
1×BFF6-0.1% Tween-20
20 U/mL Klenow (exo-)
2 U/mL Apyrase
0.05 mM PPi
Total volume: 20 μL
Incubate at 40° C. for 10 min, 4° C. pause 6. TIPP Reaction When the PPL reaction reaches 4° C., add 5 μL of TIPP mixture having:
1×BFF6-0.1% Tween-20
16 U/mL TIPP
20 μL of mixture from step 5.
Total volume: 25 μL
Incubate at 37° C. for 5 min, 60° C. 10 min, 60° C. pause 7. Preamplification Place the samples from step 6 on the magnet kept on the hot plate and heat up to 60° C.

After the beads are separated take 2 μL of supernatant and add to the following mixture:
1×Q5U buffer
dNTPs 0.4 mM
Primer mix 4 0.1 μM
Q5U polymerase 20 U/mL
UDG 10 U/mL
Total volume: 12.5 μL
Q5U buffer Primer mix 4 consists of:

```
Forward primer (SEQ ID 54):
5'-AATGATACGGCGACCACCGAGATCTACAC-3'

Reverse primer (SEQ ID 55):
5'-AATGATACGGCGACCACCGAGATCTACAC-3'
```

Place sample in the thermocycler and incubate with lid on 105° C.
1. UDG 37° C. 1 min
2. Int.denaturation 98° C. 1 min
3. Denaturation 98° C. 10 sec
4. Annealing 63° C. 15 sec
5. Elongation 72° C. 15 sec
6. Final elongation 72° C. 5 min
7. Cool down 4° C. hold
Step 3-5 repeated 12×

8. dPCR Quantification

After preamplification from step 7 is finished. Add 2 μL of mixture from step 7 to the reaction containing the following:
1×Q5U buffer
dNTPs 0.4 mM
Primer mix 5 or 6 0.2 μM
Q5U polymerase 20 U/mL
EvaGreen dye 2×
Alexa Fluor 700 dye 0.0003 μg/μL
TWEEN20 0.2%
Total volume: 12 4

Primer mix 5 has:

```
Forward primer (SEQ ID 56):
5'-TGGTAATTACCGACGAAAACGGC-3'

Reverse primer (SEQ ID 57):
5'-ACGCGTGGTTACAGTCTTGCG-3'
```

Primer mix 6 has:

```
Forward primer (SEQ ID 58):
5'-TGATTTCCGTGCGTCTGAATGC-3'

Reverse primer (SEQ ID 59):
5'-ATGCTGCCGTAGCGTGTTTCG-3'
```

Place sample in the QIAcuity Digital PCR System with lid on 105° C.
1. Int.denaturation 98° C. 1 min
2. Denaturation 98° C. 10 sec
3. Annealing 63° C. 15 sec
4. Elongation 72° C. 15 sec
5. Final elongation 72° C. 5 min
6. Cool down 35° C. 1 min
Step 2-4 repeated 30×

Figure 8:
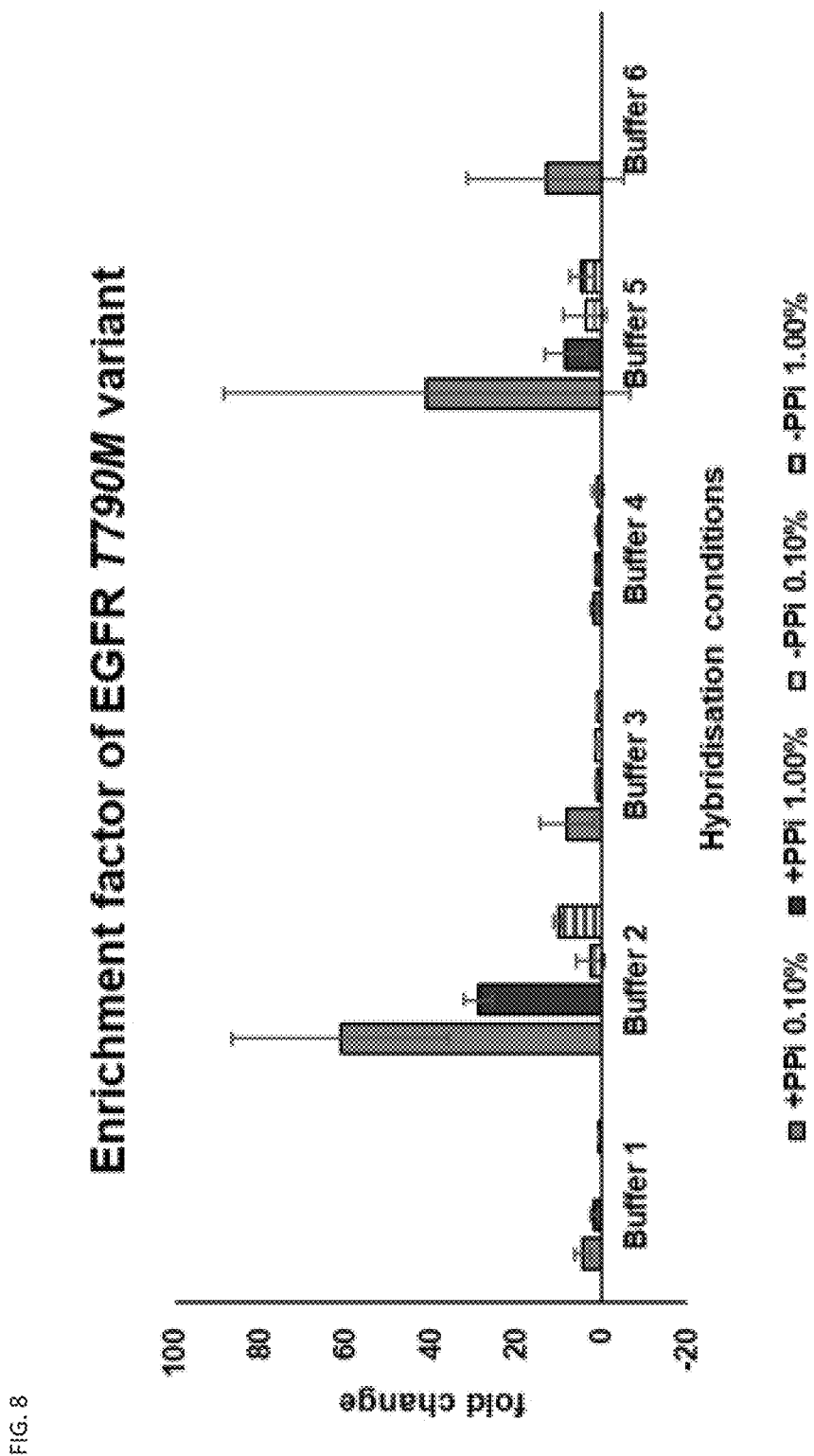
FIG. 8: Enrichment factor for the EGFR exon 20 T790M variant. Graph shows the enrichment factor for 0.1 and 1% VAF and its dependency on which buffer is used during the hybridisation step. Increase in the enrichment factor is dependent on the presence of PPi. The highest enrichment factor is achieved with Buffer 2 and buffer 5 (see Example 3).

Take a picture of the partitions in green and yellow channels with exposure duration 600 and 700 ms respectively and gain 6 and 8 respectively. Data obtained from such an experiment is shown in FIG. 8.

The invention claimed is:

1. A method for increasing the ratio of a first nucleic acid sequence to a second nucleic acid sequence in a sample, wherein the sample comprises the first and second nucleic acid molecules, the method comprising the steps of:
  a. introducing the sample comprising one or more nucleic acid analytes to a first reaction mixture comprising:
    i. a single-stranded probe oligonucleotide $A_0$ wherein said probe has greater complementarity to one of the first or second nucleic acid molecules relative to the other of the first or second nucleic acid molecules;
  b. introducing the reaction mixture produced by step (a) to a second reaction mixture comprising:
    i. a pyrophosphorolysing enzyme; and
    ii. a source of pyrophosphate ion
    wherein $A_0$ anneals better to one of the nucleic acid molecules relative to the other of the nucleic acid molecules to create an at least partially double-stranded intermediate product in which $A_0$ forms a double-stranded complex with said nucleic acid molecule and $A_0$ is pyrophosphorolysed in the 3'-5' direction from its 3'-end, whilst any $A_0$ that has annealed to a lesser degree to the other nucleic acid relative to said nucleic acid molecule is pyrophosphorolysed in the 3'-5' direction to a lesser extent relative to $A_0$ that is hybridized to said nucleic acid molecule;
  c. separating $A_0$ sequence complexes formed with said nucleic acid molecule by:
    i. allowing the strands of said complex to separate as a consequence of the pyrophosphorolysis reaction; or
    ii. heating the reaction mixture to a temperature sufficient for the stands of said complex to separate but which is below the temperature required for the stands of any $A_0$ which annealed to the other nucleic acid sequence to separate; and
  d. separating $A_0$, and thereby any nucleic acid sequences remaining annealed thereto, from any nucleic acid sequences not annealed to $A_0$.

2. The method of claim 1 wherein the separation in step (d) is performed through capture of $A_0$ onto a solid support prior to, or following, step (a).

3. The method of claim 1 wherein $A_0$ further comprises a 5' tail region which is not complementary to either of the first nucleic acid sequence or the second nucleic acid sequence.

4. The method of claim 2 wherein the capture onto the solid support is performed through hybridisation of a 5' tail region of $A_0$, which is not complementary to either of the first nucleic acid sequence or the second nucleic acid sequence, to another oligo, $C_0$, which comprises a capture moiety through which it is bound to the solid support either before or after hybridisation to $A_0$.

5. The method of claim 2 wherein $A_0$ further comprises a capture moiety through which it is bound to the solid support.

6. The method of claim 2 wherein the solid support is a bead.

7. The method of claim 6 wherein the bead is a magnetic or paramagnetic bead.

8. A method for altering the ratio of a first nucleic acid molecule to a second nucleic acid molecule in a sample, wherein the sample comprises at least the first and second nucleic acid molecules, the method comprising the steps of:
  a. introducing the sample comprising one or more nucleic acid analytes to a first reaction mixture comprising:
    i. a single-stranded probe oligonucleotide $A_0$ wherein the probe has greater complementarity to a first nucleic acid molecule relative to a second nucleic acid molecule;
    ii. a pyrophosphorolysing enzyme; and
    iii. a source of pyrophosphate ion;
    wherein $A_0$ anneals better to the first nucleic acid molecule relative to the second nucleic acid molecule to create an at least partially double-stranded intermediate product in which the 3' end of $A_0$ forms a double-stranded complex with said first nucleic acid molecule and $A_0$ is pyrophosphorolysed in the 3'-5' direction from its 3' end, whilst any $A_0$ that has annealed to the second nucleic acid molecule is pyrophosphorolysed in the 3'-5' direction to a lesser extent relative $A_0$ that annealed to first nucleic acid molecule;
  b. selectively denaturing any shortened $A_0$ sequence complexes which were annealed to the first nucleic acid molecule; and
  c. separating $A_0$, and thereby any second nucleic acid sequences remaining annealed thereto, from the first nucleic acid sequences not annealed to $A_0$, thereby altering the ratio of the first nucleic acid molecule to the second nucleic acid molecule.

9. A method for increasing the ratio of a first nucleic acid sequence to a second nucleic acid sequence in a sample, wherein the sample comprises the first and second nucleic acid molecules, the method comprising the steps of:
  a. introducing the sample comprising one or more nucleic acid analytes to a first reaction mixture comprising:
    i. a single-stranded probe oligonucleotide $A_0$ wherein said probe has greater complementarity to one of the first or second nucleic acid molecules relative to the other of the first or second nucleic acid molecules;
    ii. a pyrophosphorolysing enzyme; and
    iii. a source of pyrophosphate ion;
    wherein $A_0$ anneals better to one of the nucleic acid molecules relative to the other of the nucleic acid molecules to create an at least partially double-stranded intermediate product in which $A_0$ forms a double-stranded complex with said nucleic acid molecule and $A_0$ is pyrophosphorolysed in the 3'-5' direction from its 3'-end, whilst any $A_0$ that has annealed to a lesser degree to the other nucleic acid relative to said nucleic acid molecule is pyrophosphorolysed in the 3'-5' direction to a lesser extent relative to $A_0$ that is hybridized to said nucleic acid molecule;
  b. separating $A_0$ sequence complexes formed with said nucleic acid molecule which were annealed by:
    i. allowing the strands of said complex to separate as a consequence of the pyrophosphorolysis reaction; or ii. heating the reaction mixture to a temperature sufficient for the stands of said complex to separate but which is below the temperature required for the stands of any $A_0$ which annealed to a lesser degree to the other nucleic acid sequence to separate; and
c. separating $A_0$, and thereby any nucleic acid sequences remaining annealed thereto, from any nucleic acid sequences not annealed to $A_0$.

* * * * *